United States Patent
Takano et al.

(10) Patent No.: US 6,632,813 B1
(45) Date of Patent: Oct. 14, 2003

(54) 6-SUBTITUTED-7-HETEROQUINOXALINECARBOXYLIC ACID DERIVATIVES AND ADDITION SALTS THEREOF AND PROCESSES FOR THE PREPARATION OF BOTH

(75) Inventors: Yasuo Takano, Kazo (JP); Futoshi Shiga, Oyama (JP); Tsuyoshi Anraku, Koga (JP); Kazunori Fukuchi, Hanyu (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/926,057

(22) PCT Filed: Feb. 25, 2000

(86) PCT No.: PCT/JP00/01076

§ 371 (c)(1), (2), (4) Date: Aug. 22, 2001

(87) PCT Pub. No.: WO00/50420

PCT Pub. Date: Aug. 31, 2000

(30) Foreign Application Priority Data

Feb. 26, 1999 (JP) ............................................. 11-050238
Feb. 18, 2000 (JP) ........................................ 2000-041813

(51) Int. Cl.⁷ .................. C07D 247/02; C07D 403/04; C07D 403/06; A61K 31/498
(52) U.S. Cl. ................... 514/228.2; 514/234.8; 514/249; 544/354; 544/62; 544/116; 544/119; 544/328; 544/331
(58) Field of Search .......................... 544/354, 62, 116, 544/119, 328; 514/249, 222.8, 234.8

(56) References Cited

U.S. PATENT DOCUMENTS 5,612,354 A * 3/1997 Sanz et al. ................... 514/314
6,277,850 B1 * 8/2001 Lubisch et al. ............. 514/249
6,348,461 B1 * 2/2002 Takano et al. ............... 544/354

FOREIGN PATENT DOCUMENTS

| JP | 7-165756 | 6/1995 |
| WO | WO 92/11245 | 7/1992 |
| WO | WO 94/26737 | 11/1994 |
| WO | WO 99/11632 | 3/1999 |

* cited by examiner

Primary Examiner—Mark L. Berch
(74) Attorney, Agent, or Firm—Oblon, Spivak, McClelland, Maier & Neustadt, P.C.

(57) ABSTRACT

The invention provides compounds with antagonism against excitatory amino acid receptors, in particular, AMPA receptor having 6-substituted-7-heteroquinoxalinecarboxylic acid derivatives and addition salts thereof as effective ingredients, and processes for the preparation of both. The compounds are 6-substituted-7-heteroquinoxalinecarboxylic acid derivatives represented by the formula (1)

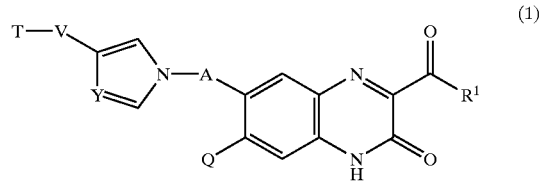

where A denotes a single bond or methylene (CH₂), Y denotes a nitrogen atom or =CH—, V denotes a single bond or methylene (CH₂), T denotes a hydroxyl group, amino group, lower alkoxycarbonyl group, carboxyl group, aldehyde group or the like, Q denotes a halogen atom, lower alkyl group or lower alkoxy group, and R¹ denotes a hydroxyl group, lower alkoxy group or the like, and addition salts thereof.

16 Claims, No Drawings

6-SUBTITUTED-7-HETEROQUINOXALINECARBOXYLIC ACID DERIVATIVES AND ADDITION SALTS THEREOF AND PROCESSES FOR THE PREPARATION OF BOTH

TECHNICAL FIELD

The present invention relates to 6-substituted-7-heteroquinoxalinecarboxylic acid derivatives and their addition salts effective for the therapy of disorder of cerebral nerve cells as antagonists against excitatory amino acid receptors, in particular, as selective antagonists against AMPA receptor in non-NMDA receptor, processes for the preparation of both, and a medicinal composition containing these compounds.

BACKGROUND TECHNOLOGIES

The glutamic acid being excitatory amino acid is a main excitatory transmitter substance in the central nervous system of vertebrates, and is known as an amino acid contained most rich in brain. It is known, however, that, when releasing from nervous axon terminals exceeding the physiological threshold, it excessively excites the glutamic acid receptor of post-synapse to cause the death of nerve cells. This is called excitotoxicity.

In recent years, it has been clarified that the death of nerve cells due to glutamic acid concerns deeply in various diseases of cerebral nerve such as cerebral hemorrhage, head trauma, epilepsy, Huntington's disease, Parkinson's disease, amyotrophic lateral sclerosis and Alzheimer's disease. It is considered therefore that, if such excitotoxicity could be prevented effectively, a potential to the therapy for these intractable diseases, for which there are virtually no therapeutic means at present, would be opened.

Roughly classifying, the glutamic acid receptor is divided into ion channel type receptor and G protein-binding type receptor, and this ion channel type receptor is further divided into NMDA (N-methyl-D-aspartic acid) receptor and non-NMDA receptor. Moreover, the latter non-NMDA receptor is classified into AMPA (α-amino-3-hydroxy-5-methyl-4-isoxazolpropionic acid) receptor and KA (kainic acid) receptor. Studies on these excitatory amino acid receptors are being put forward, and, above all, with the drug with antagonism against AMPA receptor in non-NMDA receptor, it is known that the adverse effects (learning and memory disturbances, schizophrenia-like symptom, etc.), which the drugs (MK-801 etc.) with antagonism against NMDA receptor have, are not expressed (Neurosci. Biobehav. Rev., 1992, 16, 13–24; J. Pharmacol. Exp. Ther., 1958, 245, 969–974), and that the protective effect on cerebral nerve can be expected even by the administration after ischemia (Science, 1990, 247, 571–574).

Moreover, with the compounds with quinoxalinedione structure and with antagonism against AMPA receptor such as NBQX, drawbacks of causing kidney disturbance that is considered based on physicochemical properties, and the like are reported (J. Cereb. Blood Flow Metab., 1994, 14, 251–261), hence they cannot be said to be satisfactory compounds.

Now, as the compounds with similar structure to quinoxalinecarboxylic acid derivatives, compounds represented by a general formula (15)

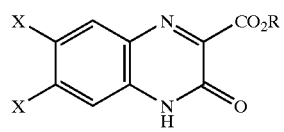

(15)

(wherein X independently denotes chlorine or bromine atom, and R denotes methyl or ethyl group), described in Jpn. Kokai Tokkyo Koho JP 56,005,416 as compounds with antiviral function by Lily Co., and compounds represented by a general formula (16)

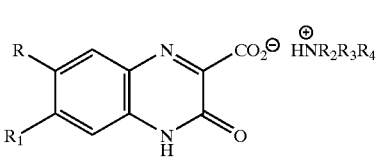

(16)

(wherein R and $R_1$ independently denote halogen atoms, $R_2$ denotes hydrogen, methyl or ethyl group, $R_3$ denotes hydrogen, methyl, ethyl, hydroxyethyl, benzyl or ethoxycarbonylmethyl group, and $R_4$ denotes cyclooctyl, norbonyl group, etc.), described in Jpn. Kokai Tokkyo Koho JP 56,081,569 as compounds with antiviral function similarly by Lily Co., are known. However, these compounds have 6- and 7-positions of symmetric type, it is not known that they have the antagonism against AMPA receptor in excitatory amino acid receptors of the inventive compounds, and they have different structure from that of the inventive compounds.

Furthermore, compounds represented by a general formula (17)

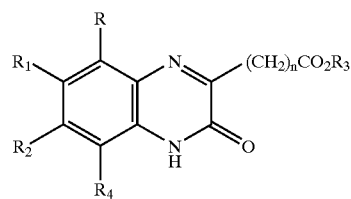

(17)

(wherein R and $R_4$ independently denote hydrogens, nitro or methoxy groups, $R_1$ and $R_2$ independently denote hydrogens, nitro or methoxy groups or halogen atoms (one of R, $R_1$, $R_2$ and $R_4$ is a group other than hydrogen, in the case of $R_1$ and $R_2$ being not nitro groups or methoxy groups, $R_1$ and $R_2$ are independently halogen atoms together and R and $R_4$ are hydrogens, and, in the case of one of R, $R_1$, $R_2$ and $R_4$ is nitro group, either one of $R_1$ and $R_2$ is methoxy group), $R_3$ denotes hydrogen, lower alkyl group which may be substituted with halogen, lower cycloalkyl group, lower alkenyl group or 2-chloroethyl group, and n denotes 0 or 2), described in Jpn. Kokai Tokkyo Koho JP 55,069,514 as compounds with antiviral function similarly by Lily Co., are known. However, disclosed compounds have different structure from that of the inventive compounds, and it is not described that they have the antagonism against AMPA receptor in excitatory amino acid receptors which the inventive compounds have.

Moreover, in WO92-11245 described by Warner-Lambert Co., as compounds with antagonism against excitatory amino acid receptor, compounds represented by a general formula (18)

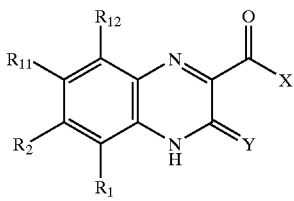
(18)

(wherein Y denotes oxygen, sulfur or nitrogen atom, $R_1$, $R_2$, $R_{11}$ and $R_{12}$ denote hydrogens, lower alkyl groups which may be substituted with halogen, halogen atoms, trifluoromethyl groups, cyano groups, nitro groups, methylthio groups, lower alkenyl groups, lower alkynyl groups, sulfonamide groups, etc., or arbitrary two of $R_1$, $R_2$, $R_{11}$ and $R_{12}$ may form a ring (6-membered ring or heterocycle which may contain heteroatom), and X denotes sulfonylamide group which may have substituents, etc.) are known. However, in these compounds, those with asymmetric substituents at 6- and 7-position of quinoxaline as the inventive compounds are not disclosed, and, with disclosed compounds, the antagonism against AMPA is not shown and the disclosed antagonism against glycine is not considered to be sufficient as well.

The invention is to provide compounds with antagonism against receptors of glutamic acid that is considered to be an etiology bringing about the memory disorder and dementia due to said diseases and selective death of cells, in particular, with high affinity and selectivity against AMPA receptor in non-NMDA receptor and protective effect on cerebral nerve cells.

DISCLOSURE OF THE INVENTION

As a result of diligent studies exploring an antagonist against excitatory amino acid receptors effective for the therapy of disorder of cerebral nerve cells, in particular, a selective antagonist against AMPA receptor in non-NMDA receptor, aiming at the development of novel therapeutic agent for the disorder of cerebral nerve cells, the inventors have found that the inventive 6-substituted-7-heteroquinoxalinecarboxylic acid derivatives and addition salts thereof have excellent antagonism against AMPA receptor.

Namely, according to the invention, it has been found that 6-substituted-7-heteroquinoxalinecarboxylic acid derivatives represented by a general formula (1)

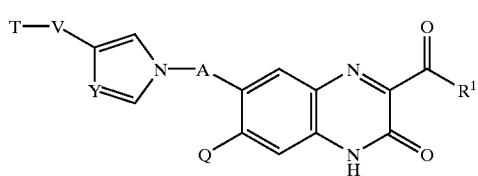
(1)

(wherein A denotes a single bond or methylene ($CH_2$),

Y denotes a nitrogen atom or =CH—,

V denotes a single bond or methylene ($CH_2$),

T denotes a hydroxyl group, amino group, lower alkoxycarbonyl group, carboxyl group, aldehyde group, general formula (2)

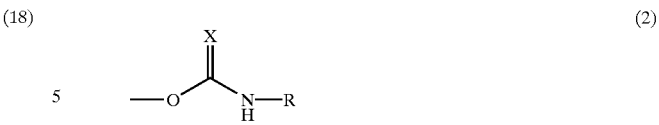
(2)

(wherein X denotes an oxygen atom or sulfur atom, R denotes an aralkyl group, phenyl group, naphthyl group, 5- or 6-membered heterocycle and its condensed ring (these may have one or more substituents on aromatic ring or heterocycle), lower alkyl group which may be substituted with halogen atom, or cycloalkyl group), or general formula (3)

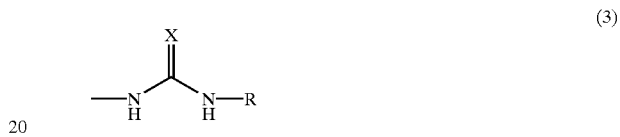
(3)

(wherein X denotes an oxygen atom or sulfur atom, R denotes an aralkyl group, phenyl group, naphthyl group, 5- or 6-membered heterocycle and its condensed ring. (these may have one or more substituents on aromatic ring or heterocycle), lower alkyl group which may be substituted with halogen atom, or cycloalkyl group), Q denotes a halogen atom, lower alkyl group or lower alkoxy group, and $R^1$ denotes a hydroxyl group or lower alkoxy group), and addition salts thereof have excellent antagonism against AMPA receptor, leading to the completion of the invention.

In the general formula (1) of the inventive compounds, preferably, compounds, $R^1$ being hydroxyl group or ethoxy group and A being single bond, are mentioned. More preferably, compounds, Q being chloro group, $R^1$ being hydroxyl group, V being methylene ($CH_2$), X being oxygen atom and R being 4-carboxyphenyl group in the general formula (2) and general formula (3) for T are mentioned.

As these preferable compounds, compounds shown below, namely, ethyl 6-chloro-3,4-dihydro-7-(3-formylpyrrole-1-yl)-3-oxoquinoxaline-2-carboxylate, ethyl 3,4-dihydro-7-(3-formylpyrrole-1-yl)-6-methoxy-3-oxoquinoxaline-2-carboxylate, ethyl 7-(3-formylpyrrole-1-yl)-6-methyl-3-oxo-1,2,3,4-tetrahydroquinoxaline-2-carboxylate, ethyl 7-(3-formylpyrrole-1-yl)-6-fluoro-3-oxo-1,2,3,4-tetrahydroquinoxaline-2-carboxylate, ethyl 7-(3-(aminomethyl)pyrrole-1-yl)-6-chloro-3-oxo-1,2,3,4-tetrahydroquinoxaline-2-carboxylate hydrochloride, ethyl 6-chloro-7-(3-(((4-ethoxycarbonylphenyl)aminocarbonylamino)methyl)pyrrole-1-yl)-3-oxo-1,2,3,4-tetrahydroquinoxaline-2-carboxylate, ethyl 6-chloro-3,4-dihydro-7-(3-(((4-ethoxycarbonylphenyl)aminocarbonylamino)methyl)pyrrole-1-yl)-3-oxoquinoxaline-2-carboxylate, ethyl 6-chloro-3,4-dihydro-7-(3-(((4-ethoxycarbonyl-2-fluorophenyl)aminocarbonylamino)methyl)pyrrole-1-yl)-3-oxoquinoxaline-2-carboxylate, 7-(3-(((4-carboxyphenyl)aminocarbonylamino)methyl)pyrrole-1-yl)-6-chloro-3,4-dihydro-3-oxoquinoxaline-2-carboxylic acid, 7-(3-(((4-carboxyphenyl)aminocarbonylamino)methyl)pyrrole-1-yl)-3,4-dihydro-6-methyl-3-oxoquinoxaline-2-carboxylic acid, 7-(3-(((4-carboxyphenyl)aminocarbonylamino)methyl)pyrrole-1-yl)-3,4-dihydro-6-methoxy-3-oxoquinoxaline-2-carboxylic acid, 7-(3-(((4-carboxyphenyl)aminocarbonylamino)methyl)pyrrole-1-yl)-3,4-dihydro-6- fluoro-3-oxoquinoxaline-2-carboxylic acid, 7-(3-(((4-carboxy-2-fluorophenyl)aminocarbonylamino)methyl) pyrrole-1-yl)-6-chloro-3,4-dihydro-3-oxoquinoxaline-2-carboxylic acid, ethyl 6-chloro-3,4-dihydro-7-(4-(hydroxymethyl)imidazole-1-yl)-3-oxoquinoxaline-2-carboxylate, ethyl 6-chloro-3,4-dihydro-7-(4-(((4-ethoxycarbonylphenyl)carbamoyloxy)methyl)imidazole-1-yl)-3-oxoquinoxaline-2-carboxylate, ethyl 6-chloro-3,4-dihydro-7-(4-(((4-ethoxycarbonylmethylphenyl) carbamoyloxy)methyl)imidazole-1-yl)-3-oxoquinoxaline-2-carboxylate, 7-(4-(((4-carboxyphenyl)carbamoyloxy) methyl)imidazole-1-yl)-6-chloro-3,4-dihydro-3-oxoquinoxaline-2-carboxylic acid, 7-(4-(((4-carboxy-2-fluorophenyl)carbamoyloxy)methyl)imidazole-1-yl)-6-chloro-3,4-dihydro-3-oxoquinoxaline-2-carboxylic acid, 7-(4-(((4-carboxyphenyl)aminocarbonylamino)methyl) imidazole-1-yl)-6-chloro-3,4-dihydro-3-oxoquinoxaline-2-carboxylic acid, 7-(4-(((4-carboxy-2-fluorophenyl) aminocarbonylamino)methyl)imidazole-1-yl)-6-chloro-3,4-dihydro-3-oxoquinoxaline-2-carboxylic acid, 7-(4-(((4-carboxymethylphenyl)aminocarbonylamino)methyl) imidazole-1-yl)-6-chloro-3,4-dihydro-3-oxoquinoxaline-2-carboxylic acid, and the like can be mentioned.

Best Embodiment to Put the Invention Into Practice

In the description of the general formula (1) of the invention, "for substituents" in the phrase of "aralkyl group, phenyl group, naphthyl group, 5- or 6-membered heterocycle and its condensed ring (these may have one or more substituents on aromatic ring or heterocycle)", halogen atom, hydroxyl group, lower alkyl group which may be substituted with halogen atom, lower alkoxy group, lower alkylthio group, lower alkoxycarbonyl group, nitro group, amino group which may be substituted, cyano group, carboxyl group, aldehyde group, lower alkanoic acid group, etc. are mentioned, for "lower alkyl groups", straight chain or branched ones with carbon atoms of 1 to 6 such as methyl, ethyl, n-propyl and iso-propyl are mentioned, for "cycloalkyl groups", ones with carbon atoms of 3 to 7 such as cyclopropyl, cyclopentyl and cyclohexyl are mentioned, for "halogen atoms", fluorine, chlorine, bromine and iodine are mentioned, "lower alkoxy groups", straight chain or branched ones with carbon atoms of 1 to 4 such as methoxy, ethoxy and propoxy are mentioned, for "lower alkylthio groups", straight chain or branched ones with carbon atoms of 1 to 6 such as methylthio, ethylthio and propylthio are mentioned, for "lower alkoxycarbonyl groups", straight chain or branched ones with carbon atoms of 1 to 4 such as methoxycarbonyl and ethoxycarbonyl are mentioned, and, for "amino groups which may be substituted", amino groups may be substituted with acyl group or arylsulfonyl group, for example, acetyl, methanesulfonyl, phenylsulfonyl, etc., or they may be substituted with lower alkyl group which may be substituted with 1 to 2 halogen atoms, phenyl group which may have 1 to 2 substituents or aralkyl group which may have 1 to 2 substituents. The substituents referred to so here are "substituents" as described above.

Furthermore, in the description, "heterocycles" in the phrase of "aralkyl group, phenyl group, naphthyl group, 5- or 6-membered heterocycle and its condensed ring (these may have one or more substituents on aromatic ring or heterocycle)" are saturated or unsaturated monocyclic or polycyclic heterocycle groups which may have one or more substituents and which can contain one or more nitrogen, oxygen or sulfur atoms, and, for example, pyrrolidyl, piperidyl, piperazyl, morpholyl, thiomorpholyl, furanyl, thienyl, pyrazolyl, imidazolyl, oxazolyl, thiazolyl, pyridyl, pyrimidyl, pyridazyl, pyrazyl, etc. are mentioned. "Its condensed ring" represents benzene-condensed rings of said "heterocycles" and, for example, indolyl, tetrahydroquinolyl, benzoxazolidinyl, benzothiazolidinyl, benzofuranyl, benzothienyl, benzimidazolyl, quinolyl, isoquinolyl, quinazolyl, quinoxalyl, cinnolyl, etc. are mentioned.

The compounds of the invention are prepared, for example, through preparative processes shown below.

Compounds represented by the general formula (1) can be synthesized by reacting compounds represented by a general formula (4)

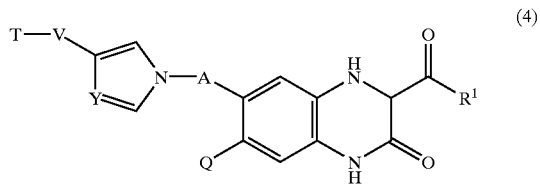

(4)

(wherein A, Y, V, T, Q and $R^1$ are as described above), for 1 to 24 hours at 20 to 120° C. in a suitable solvent, for example, tetrahydrofuran, dioxane, N,N-dimethylformamide, N,N-dimethylacetamide, N-methylpyrrolidone, acetonitrile, benzene, toluene or the like, using an oxidizing agent, for example, DDQ (dichlorodicyanoquinone). They can also be synthesized by reacting compounds represented by the general formula (4) for 1 to 24 hours at 20 to 120° C. in a suitable solvent, for example, tetrahydrofuran, dioxane, N,N-dimethylformamide, N,N-dimethylacetamide, N-methylpyrrolidone, acetonitrile, benzene, toluene, ethanol, methanol or the like, using an organic base, for example, triethylamine, ethyldiisopropylamine or the like, or an inorganic base, for example, potassium carbonate, sodium carbonate, potassium hydroxide or sodium hydroxide. Moreover, compounds represented by the general formula (1) can be obtained by reacting compounds represented by a general formula (5)

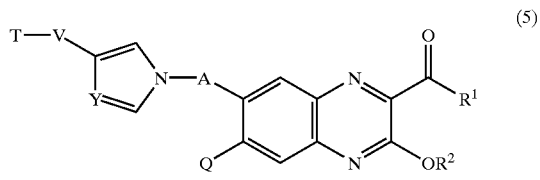

(5)

(wherein A, Y, V, T, Q and $R^1$ are as described above, and $R^2$ denotes a lower alkyl group which may be substituted with halogen atom or aralkyl group which may have one or more substituents), for 0.5 to 72 hours at 20 to 120° C. without solvent or in a suitable solvent, for example, water, acetic acid, methanol or the like, using a suitable acid, for example, hydrochloric acid, sulfuric acid, hydrobromic acid, trifluoroacetic acid, mixed acid thereof or the like to synthesize compounds, $R^1$ in the general formula (1) being hydroxyl group alkoxy group among compounds represented by the general formula (5), those compounds are reacted for 0.5 to 72 hours at 20 to 120° C. without solvent or in a suitable solvent, for example, water, acetic acid, methanol or the like, using a suitable acid, for example, hydrochloric acid, sulfuric acid, hydrobromic acid, trifluoroacetic acid or the like to deprotect $R^2$, and then reacted for 0.5 to 10 hours at 20 to 100° C. in a solvent of water, methanol, ethanol or the like, using a suitable alkali, for example, potassium hydroxide, sodium hydroxide or the like to synthesize compounds, $R^1$ in the general formula (1) being hydroxyl group.

Moreover, compounds, $R^1$ being lower alkoxy group among compounds represented by the general formula (1), can be obtained by reacting those compounds for 0.5 to 10 hours at 20 to 100° C. in a suitable solvent of water, methanol, ethanol or the like, using a suitable alkali, for example, potassium hydroxide, sodium hydroxide or the like to synthesize compounds, $R^1$ in the general formula (1) being hydroxyl group.

Moreover, compounds, Y being represented by =CH— among compounds represented by the general formula (1), can also be synthesized by reacting compounds represented by a general formula (6)

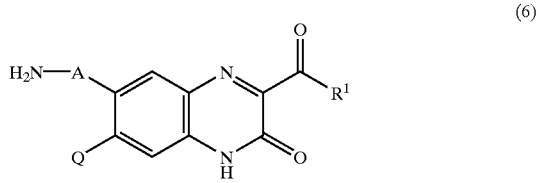

(6)

(wherein A, Q and $R^1$ are as described above), with compounds represented by a general formula (7)

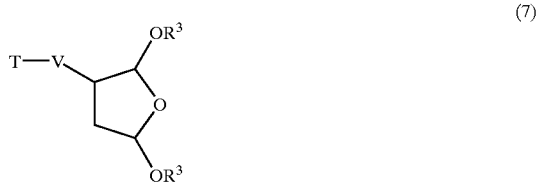

(7)

(wherein T and V are as described above, and $R^3$ denotes a lower alkyl group which may be substituted with halogen atom or aralkyl group which may have one or more substituents), for 0.5 to 5 hours at 20 to 120° C. without solvent or in a suitable solvent such as tetrahydrofuran, benzene, toluene, acetic acid, ethanol, methanol or the like (suitable inorganic or organic acid, for example, hydrochloric acid, sulfuric acid, p-toluene sulfonic acid or the like may be added).

Moreover, compounds, T being represented by the general formula (2) or general formula (3) among compounds represented by the general formula (1), can also be synthesized by reacting compounds represented by a general formula (8)

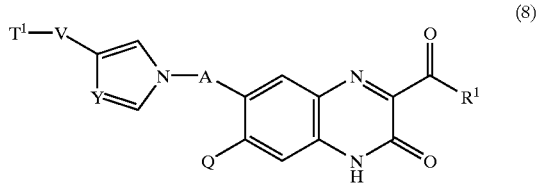

(8)

(wherein $T^1$ denotes hydroxyl group or amino group, and A, Y, V, Q and $R^1$ are as described above), with compounds represented by a general formula (9)

Z—N=C=Xa (9)

(wherein Z denotes an aralkyl group, phenyl group, naphthyl group, 5- or 6-membered heterocycle and its condensed ring (these may have one or more substituents on aromatic ring or heterocycle), lower alkyl group which may be substituted with halogen atom or cycloalkyl group, and Xa denotes an oxygen or sulfur atom), for 0.5 to 24 hours at 20 to 120° C. in a suitable solvent, for example, tetrahydrofuran, dioxane, N,N-dimethylformamide, N,N-dimethylacetamide, N-methylpyrrolidone, acetonitrile, benzene, toluene or the like, without base or using a suitable organic base, for example, triethylamine or the like, Moreover, they can also be synthesized by converting compounds represented by a general formula (10)

Z—$A_1$—D (10)

(wherein Z denotes an aralkyl group, phenyl group, naphthyl group, 5- or 6-membered heterocycle and its condensed ring (these may have one or more substituents on aromatic ring or heterocycle), lower alkyl group which may be substituted with halogen atom or cycloalkyl group, $A_1$ denotes single bond, and D denotes an amino group, carboxyl group, amide group or lower alkoxycarbonyl group), to isocyanic (isothiocyanic) esters or carbamic chlorides through already known process, in place of the general formula (9), and then reacting with general formula (8) similarly to general formula (9).

For example, in the case of D being amino group, they can be converted to carbamic chlorides or isocyanic (isothiocyanic) esters by reacting with phosgene (thiophosgene), phosgene dimer (2,2,2-trichloromethyl chloroformate) or its homologue (4-nitrophenyl chloroformate etc.) for 1 to 5 hours at −10 to 50° C. in a suitable solvent, for example, tetrahydrofuran, dioxane, benzene, toluene or the like, without base or using a suitable organic base, for example, triethylamine or the like. Further, they can be converted to isocyanic (isothiocyanic) esters by using Curtius rearrangement reaction or Schmidt rearrangement reaction after converted carboxyl group to acid azide in the case of D being carboxyl group, and by using Hofmann rearrangement reaction in the case of D being amide group. Moreover, in the case of D being carboxyl group, it is also possible to convert to isocyanic (isothiocyanic) esters in one pot using DPPA (diphenylphosphoryl azide).

Moreover, compounds represented by the general formula (1) can also be synthesized by reacting compounds represented by a general formula (11)

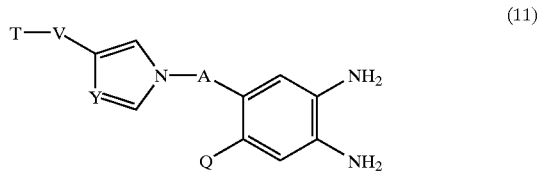

(11)

(wherein A, Y, V, T and Q are as described above), with ketomalonic diesters represented by a general formula (12)

(12)

(wherein $R^4$ denotes a lower alkyl group), for 2 to 12 hours at 25 to 100° C. in a suitable solvent, for example, ethanol, methanol, tetrahydrofuran or the like.

Moreover, compounds, Y being CH among compounds represented by the general formula (4), can also be synthesized by reacting compounds represented by a general formula (13)

(13)

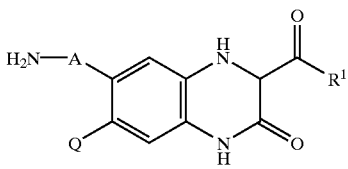

(wherein A, Q and $R^1$ are as described above), with compounds represented by the general formula (7)

(7)

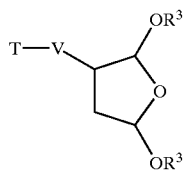

(wherein T, V and $R^3$ are as described above), for 0.5 to 5 hours at 20 to 120° C. without solvent or in a suitable solvent such as tetrahydrofuran, benzene, toluene, acetic acid, ethanol, methanol or the like (suitable inorganic or organic acid, for example, hydrochloric acid, sulfuric acid, tosyl acid or the like may be added).

Moreover, compounds, T being represented by the general formula (2) or general formula (3) among compounds represented by the general formula (4), can also be synthesized by reacting compounds represented by a general formula (14)

(14)

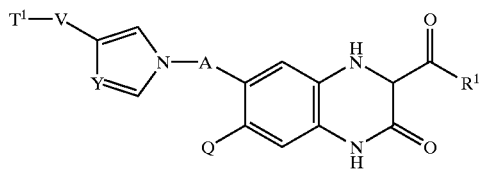

(wherein A, Y, V, $T^1$, Q and $R^1$ are as described above), with compounds represented by the general formula (9)

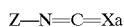 (9)

(wherein Z and Xa are as described above), for 1 to 24 hours at 20 to 120° C. in a suitable solvent, for example, tetrahydrofuran, dioxane, N,N-dimethylformamide, N,N-dimethylacetamide, N-methylpyrrolidone, acetonitrile, benzene, toluene or the like, without base or using a suitable organic base, for example, triethylamine or the like. Moreover, they can also be synthesized by converting compounds represented by the general formula (10)

 (10)

(wherein Z and D are as described above), to isocyanic (isothiocyanic) esters or carbamic chlorides through already known process, in place of the general formula (9), and then reacting with general formula (14) similarly to general formula (9).

For example, in the case of D being amino group, they can be converted to carbamic chlorides or isocyanic (isothiocyanic) esters by reacting with phosgene (thiophosgene), phosgene dimer (2,2,2-trichloromethyl chloroformate) or its homologue (4-nitrophenyl chloroformate etc.) for 1 to 5 hours at −10 to 50° C. in a suitable solvent, for example, tetrahydrofuran, dioxane, benzene, toluene or the like, without base or using a suitable organic base, for example, triethylamine or the like. Further, they can be converted to isocyanic (isothiocyanic) esters by using Curtius rearrangement reaction or Schmidt rearrangement reaction after converted carboxyl group to acid azide in the case of D being carboxyl group, and by using Hofmann rearrangement reaction in the case of D being amide group. Moreover, in the case of D being carboxyl group, it is also possible to convert to isocyanic (isothiocyanic) esters in one pot using DPPA (diphenylphosphoryl azide).

Moreover, compounds, Q being halogen atom among compounds represented by the general formula (5), can be synthesized by reacting compounds represented by a general formula (19)

(19)

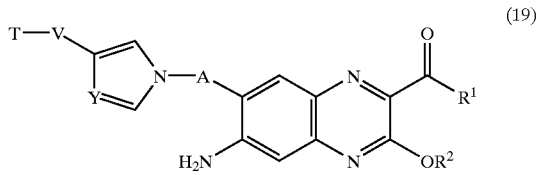

(wherein A, Y, V, T, $R^1$ and $R^2$ are as described above), with diazotizing agent, for example, sodium nitrite or the like for 0.5 to 1 hour at 0 to 50° C. in a suitable solvent, for example, acetic acid, water, mixed solvent thereof or the like, and then reacting with halogenating agent, for example, potassium chloride, potassium bromide, potassium iodide or the like for 0.5 to 2 hours at 25 to 50° C. Moreover, they can also be synthesized by reacting compounds represented by the general formula (19) with alkyl nitrite, for example, t-butyl nitrite or the like and cupper (I or II) halide, for example, cupper chloride, cupper bromide, cupper iodide or the like for 1 to 5 hours at 25 to 50° C. in a suitable solvent, for example, dimethyl sulfoxide, acetonitrile or the like.

Moreover, compounds, A being methylene ($CH_2$) among compounds represented by the general formula (5), can also be synthesized by reacting compounds represented by a general formula (20)

(20)

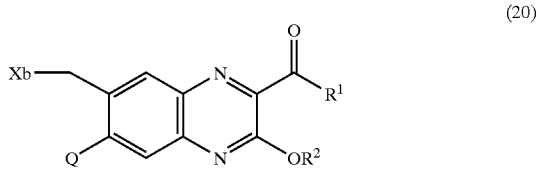

(wherein Q, $R^1$ and $R^2$ are as described above, and Xb denotes a halogen atom), with compounds represented by a general formula (21)

(21)

(wherein Y, V and T are as described above), for 2 to 10 hours at 25 to 110° C. in a suitable solvent, for example, N,N-dimethylformamide, acetonitrile or the like in the presence of an organic base, for example, triethylamine or the like.

Moreover, compounds, A being single bond among compounds represented by the general formula (6), can be synthesized by reacting compounds represented by a general formula (22)

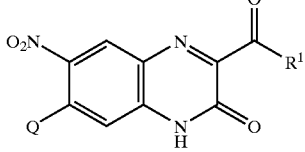
(22)

(wherein Q and R¹ are as described above), for 1 to 7 hours at 25 to 100° C. in a suitable solvent, for example, ethanol, dilute hydrochloric acid, acetic acid or mixed solvent thereof in the presence of tin chloride, zinc, iron, sodium hydrosulfite or the like.

Moreover, compounds, A being methylene (CH₂) among compounds represented by the general formula (6), can be synthesized by reacting compounds represented by a general formula (23)

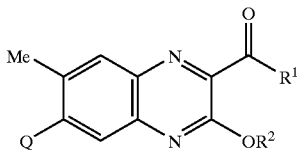
(23)

(wherein Q, R¹ and R² are as described above), for 1 to 12 hours at 20 to 100° C. in a suitable solvent, for example, carbon tetrachloride, chloroform, acetic acid or the like, using a halogenating agent, for example, N-bromosuccinimide (NBS), N-chlorosuccinimide (NCS), bromine or the like to convert to compounds represented by the general formula (20)

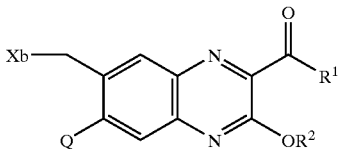
(20)

(wherein Q, R¹, R² and Xb are as described above), then by reacting these with compounds represented by a general formula (24)

(24)

(wherein R⁵ and R⁶ identically or differently denote hydrogen atoms or protective groups of amino group), for 1 to 48 hours at 20 to 160° C. in a suitable solvent, for example, tetrahydrofuran, dioxane, N,N-dimethylformamide, N,N-dimethylacetamide, N-methylpyrrolidone, acetonitrile, benzene, toluene or the like, without base or using a suitable inorganic or organic base, for example, sodium hydride, sodium carbonate, potassium carbonate, triethylamine or the like to convert to compounds represented by a general formula (25)

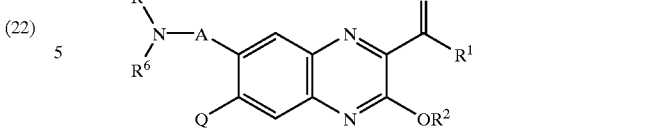
(25)

(wherein A, Q, R¹, R², R⁵ and R⁶ are as described above), and further by reacting these for 0.5 to 24 hours at 20 to 100° C. in a suitable solvent, for example, methanol, ethanol or the like, using a suitable acid, for example, hydrochloric acid, sulfuric acid or the like.

Moreover, compounds represented by the general formula (8) can be synthesized by reacting compounds represented by the general formula (14)

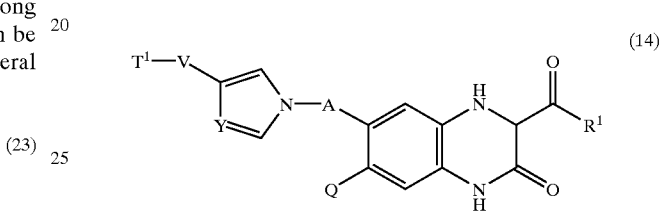
(14)

(wherein A, Y, V, T¹, Q and R¹ are as described above), for 1 to 24 hours at 20 to 120° C. in a suitable solvent, for example, tetrahydrofuran, dioxane, N,N-dimethylformamide, N,N-dimethylacetamide, N-methylpyrrolidone, acetonitrile, benzene, toluene or the like, using an oxidizing agent, for example, DDQ (dichlorodicyanoquinone).

Moreover, they can also be synthesized by reacting compounds represented by the general formula (14) for 1 to 24 hours at 20 to 120° C. in a suitable solvent, for example, tetrahydrofuran, dioxane, N,N-dimethylformamide, N,N-dimethylacetamide, N-methylpyrrolidone, acetonitrile, benzene, toluene, ethanol, methanol or the like, using an organic base, for example, triethylamine, ethyldiisopropylamine or the like or inorganic base, for example, potassium carbonate, sodium carbonate, potassium hydroxide or sodium hydroxide.

Moreover, compounds represented by the general formula (11) can be synthesized, for example, by deprotecting compounds represented by a general formula (26)

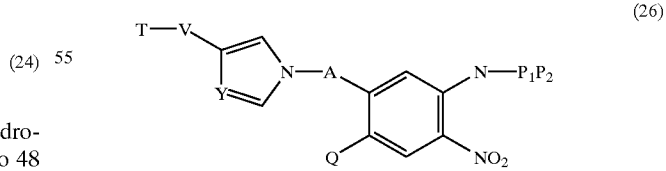
(26)

(wherein A, Y, V, T and Q are as described above, and, for P₁P₂, one denotes hydrogen atom and the other denotes protective group of amino group, or both denote protective groups of amino group), according to usual process (general formula 27), and then by reducing nitro group to convert to phenylenediamine (general formula 11).

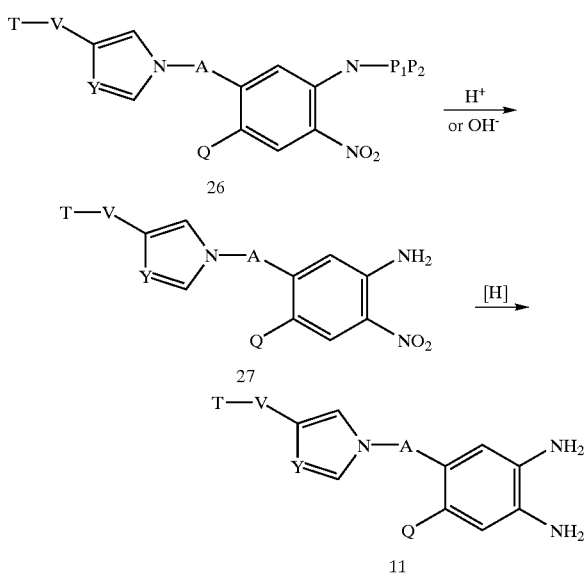

(wherein A, Y, V, T, Q, $P_1$ and $P_2$ are as described above)

The deprotection of general formula (26) can be performed by reacting for 3 to 72 hours at 20 to 120° C. without solvent or in a suitable solvent, for example, water, methanol, ethanol or the like, using a suitable acid, for example, hydrochloric acid, sulfuric acid, hydrobromic acid, trifluoroacetic acid or the like, or by reacting for 0.5 to 10 hours at 20 to 100° C. using a suitable alkali, for example, potassium hydroxide, sodium hydroxide or the like.

The reduction of nitro group of general formula (27) can also be performed through reduction by catalytic hydrogenation, that is, by hydrogenating at 25 to 80° C. and at atmospheric pressure to 5 atm (507 KPa) in a suitable solvent, for example, ethanol, methanol, acetic acid or the like in the presence of a suitable catalyst, for example, palladium on carbon, platinum oxide, rhodium on alumina or the like. Also, it can be performed by reacting at 25 to 100° C. in a suitable solvent, for example, ethanol, dilute hydrochloric acid, acetic acid or mixed solvent thereof in the presence of tin chloride, zinc, iron, sodium hydrosulfite or the like.

Moreover, compounds, A being single bond and $R^1$ being ethoxy group among compounds represented by the general formula (13), can be synthesized through processes shown by following scheme.

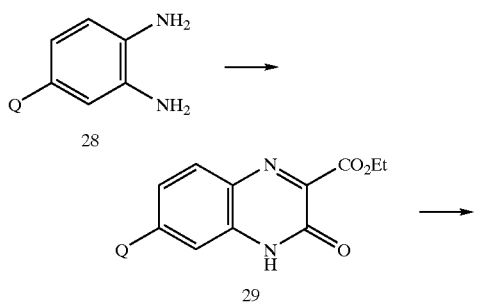

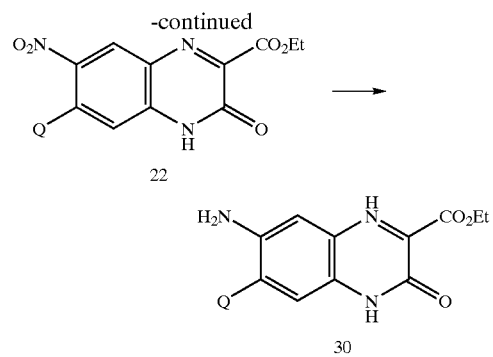

(wherein Q is as described above)

Compounds (28) synthesizable through already known process are reacted with diethyl ketomalonate for 1 to 6 hours at 20 to 120° C. in a suitable solvent, for example, ethanol, methanol, tetrahydrofuran or the like to convert to compounds (29), these compounds are subject to nitration, that is, reacted for 0.5 to 2 hours at −10 to 80° C. without solvent or in a suitable solvent, for example, concentrated sulfuric acid, carbon disulfide or acetic acid solvent, using a suitable nitrating agent, for example, concentrated nitric acid, fuming nitric acid, potassium nitrate or the like to convert to compounds represented by compounds (29), and these are reduced through catalytic hydrogenation, that is, by hydrogenating at 20 to 80° C. and at atmospheric pressure to 5 atm (507 KPa) in a suitable solvent, for example, ethanol, methanol, acetic acid or the like in the presence of a suitable catalyst, for example, palladium on carbon, platinum oxide, rhodium on alumina or the like, thus making it possible to synthesize.

Moreover, compounds represented by the general formula (14) can also be synthesized by reducing compounds represented by the general formula (8) through catalytic hydrogenation, that is, by hydrogenating at 20 to 80° C. and at atmospheric pressure to 5 atm (507 KPa) in a suitable solvent, for example, ethanol, methanol, acetic acid or the like in the presence of a suitable catalyst, for example, palladium on carbon, platinum oxide, rhodium on alumina or the like.

Moreover, compounds represented by the general formula (19) can be synthesized by reducing compounds represented by a general formula (31)

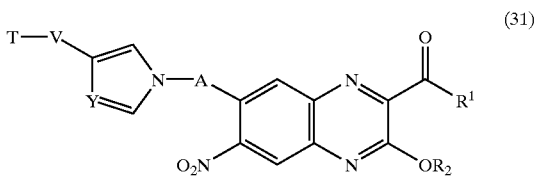

(wherein A, Y, V, T, $R^1$ and $R^2$ are as described above), through catalytic hydrogenation, that is, by hydrogenating at 20 to 80° C. and at ambient pressure to 5 atm (507 KPa) in a suitable solvent, for example, ethanol, methanol, acetic acid or the like in the presence of a suitable catalyst, for example, palladium on carbon, platinum oxide, rhodium on alumina or the like.

Moreover, compounds, A being single bond among compounds represented by the general formula (31), can be synthesized by reacting compounds represented by a general formula (32)

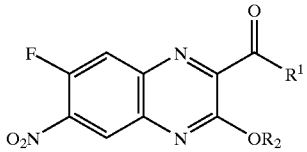

(32)

(wherein R¹ and R² are as described above), with compounds represented by the general formula (21)

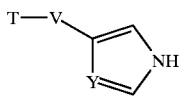

(21)

(wherein Y, V and T are as described above), for 2 to 10 hours at 25 to 150° C. in a suitable solvent, for example, N,N-dimethylformamide, acetonitrile or the like, in the presence of organic base, for example, triethylamine or the like.

Here, the general formula (23) or general formula (32) can be synthesized by reacting a general formula (33) or general formula (34)

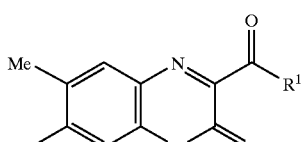

(33)

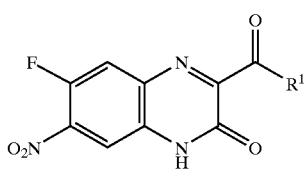

(34)

(wherein Q and R¹ are as described above), with alkyl halide, for example, methyl iodide or the like, or aralkyl halide, for example, 4-methoxybenzyl chloride or the like for 2 to 10 hours at 20 to 120° C. in a suitable solvent, for example, benzene, toluene, chloroform, methylene chloride, tetrahydrofuran or the like, using a suitable silver catalyst, for example, silver oxide, silver carbonate or the like.

Moreover, they can also be synthesized by reacting compounds represented by the general formula (33) or general formula (34) for 2 to 6 hours at 0 to 120° C. in a suitable solvent, for example, benzene, toluene, chloroform, methylene chloride, tetrahydrofuran or the like, using borate, for example, tetramethyloxonium borate or the like.

Moreover, the general formula (34) can be synthesized through synthetic processes shown by following scheme.

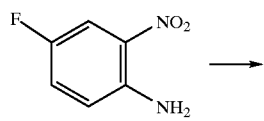

35

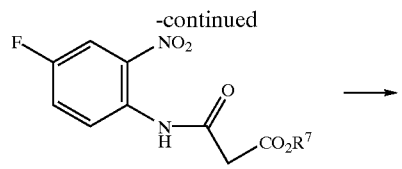

36

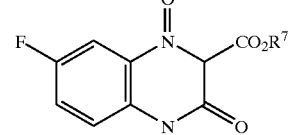

37

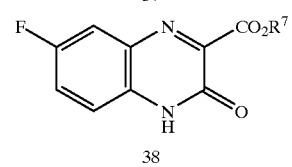

38

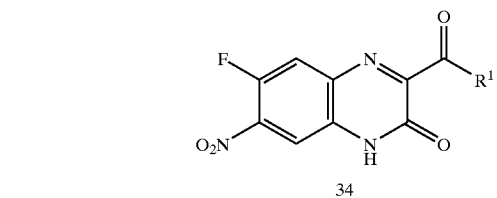

34

(R denotes a lower alkyl group)

Moreover, compounds, A being single bond among compounds represented by the general formula (26), can be synthesized through processes shown by following scheme.

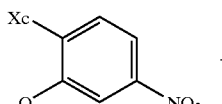

39

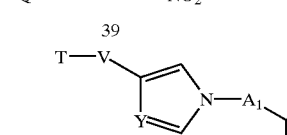

40

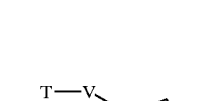

41

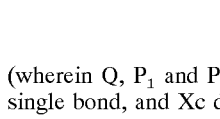

26

(wherein Q, P₁ and P₂ are as described above, A₁ denotes single bond, and Xc denotes a halogen atom)

Namely, a general formula (39) synthesizable through already known process are reacted with compounds represented by the general formula (21)

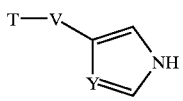
(21)

(wherein Y, T and V are as described above), for 2 to 10 hours at 25 to 150° C. in a suitable solvent, for example, N,N-dimethylformamide, acetonitrile or the like in the presence of organic base, for example, triethylamine or the like to convert to general formula (40). This general formula (40) is reduced, for example, through catalytic hydrogenation, that is, by hydrogenating at 20 to 80° C. and at atmospheric pressure to 5 atm (507 KPa) in a suitable solvent, for example, ethanol, methanol, acetic acid or the like in the presence of a suitable catalyst, for example, palladium on carbon, platinum oxide, rhodium on alumina or the like to convert to general formula (41) (if need be, amino group is protected according to usual process), and this is reacted for 0.5 to 2 hours at −10 to 80° C. without solvent or in a suitable solvent, for example, concentrated sulfuric acid, carbon disulfide, acetic acid or the like, using a suitable nitrating agent, for example, concentrated nitric acid, fuming nitric acid, potassium nitrate or the like, thus making it possible to synthesize.

Describing the examples of the inventive compounds, the invention will be illustrated in more detail.

EXAMPLE 1

Ethyl 6-Chloro-3,4-dihydro-7-(3-formylpyrrole-1-yl)-3-oxoquinoxaline-2-carboxylate

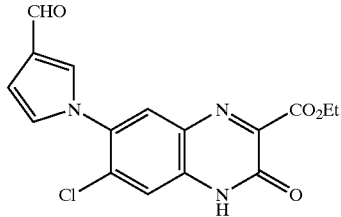

To a solution of ethyl 7-amino-6-chloro-3,4-dihydro-3-oxoquinoxaline-2-carboxylate (500mg, 1.87 mmol) in acetic acid (10 ml) was added dropwise 2,5-dimethoxytetrahydrofuran-3-aldehyde (318 μl, 2.24 mmol) at 50° C., and the mixture was stirred for 40 minutes at the same temperature. The reaction mixture was poured into water (100 ml), which was extracted with ethyl acetate. After dried over anhydrous sodium sulfate, solvent was distilled off. The residue obtained was submitted to silica gel column chromatography [ethyl acetate-hexane=3:2] to obtain 166 mg of title compound as yellowish brown oily product. Yield 26%.

1H-NMR (DMSO-d6, δ): 1.48 (3H, t, J=7.3 Hz), 4.57 (2H, q, J=7.3 Hz), 6.86 (1H, q, J=1.5 Hz), 6.93 (1H, t, J=2.4 Hz), 7.55 (1H, t, J=1.5 Hz), 7.70 (1H, s), 8.01 (1H, s), 9.90 (1H, s), 12.00–12.50 (1H, br).

EXAMPLE 2

Ethyl 3,4-Dihydro-7-(3-formylpyrrole-1-yl)-6-methoxy-3-oxoquinoxaline-2-carboxylate

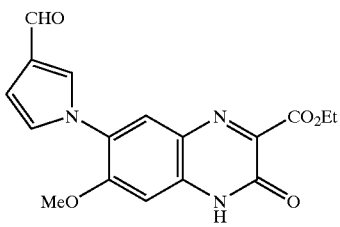

Using ethyl 7-amino-6-methoxy-3-oxo-1,2,3,4-tetrahydroquinoxaline-2-carboxylate (940 mg, 3.54 mmol) and through the process similar to Example 1, 99.1 mg of title compound were obtained as yellow powder. Yield 8%.

1H-NMR (DMSO-d6, δ): 1.31 (3H, t, J=7.3 Hz), 3.93 (3H, s), 4.36 (2H, q, J=7.3 Hz), 6.64 (1H, t, J=1.5 Hz), 7.00 (1H, s), 7.24 (1H, t, J=2.0 Hz), 7.94 (1H, s), 7.97 (1H, d, J=1.5 Hz), 9.77 (1H, s), 12.95 (1H, brs).

EXAMPLE 3

Ethyl 7-(3-Formylpyrrole-1-yl)-6-methyl-3-oxo-1,2,3,4-tetrahydroquinoxaline-2-carboxylate

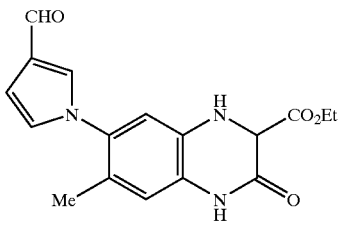

To a suspension of ethyl 7-amino-6-methyl-3-oxo-1,2,3,4-tetrahydroquinoxaline-2-carboxylate hydrochloride (1.00 g, 3.50 mmol) and sodium acetate (345 mg, 4.20 mmol) in ethanol (35 ml) was added dropwise 2,5-dimethoxytetrahydrofuran-3-aldehyde (596 μl, 4.20 mmol), and the mixture was refluxed for 3 hours. After cooling, the residue obtained by distilling off solvent was submitted to silica gel column chromatography [ethyl acetate-hexane= 3:2] to obtain 508 mg of title compound as yellowish white powder. Yield 44%.

1H-NMR (DMSO-d6, δ): 1.16 (3H, t, J=6.9 Hz), 1.98 (3H, s), 4.11 (2H, q, J=7.3 Hz), 4.61 (1H, d, J=1.5 Hz), 6.60 (1H, d, J=1.5 Hz), 6.70 (2H, s), 6.81 (1H, s), 7.01 (1H, d, J=2.0 Hz), 7.75 (1H, d, J=1.5 Hz), 9.74 (1H, s), 10.72 (1H, s).

19

EXAMPLE 4

Ethyl 6-Fluoro-7-(3-formylpyrrole-1-yl)-3-oxo-1,2,3,4-tetrahydroquinoxaline-2-carboxylate

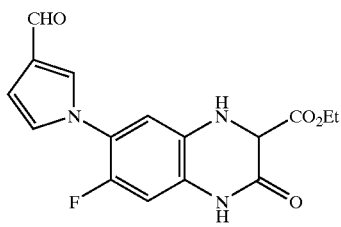

To a solution of ethyl 7-amino-6-fluoro-3-oxo-1,2,3,4-tetrahydroquinoxaline-2-carboxylate (2.03 g, 8.02 mmol) in ethanol (80 ml) was added dropwise 2,5-dimethoxytetrahydrofuran-3-aldehyde (1.36 ml, 9.62 mmol), and the mixture was refluxed for 3 hours. After cooling, the residue obtained by distilling off solvent was submitted to silica gel column chromatography [ethyl acetate-hexane=2:1] to obtain 333 mg of title compound as yellow powder. Yield 13%.

1H-NMR (DMSO-d6, δ): 1.16 (3H, t, J=7.3 Hz), 4.09–4.14 (2H, m), 4.66 (1H, d, J=2.0 Hz), 6.65 (1H, q, J=1.5 Hz), 6.78 (1H, d, J=11.7 Hz), 6.89 (1H, d, J=2.0 Hz), 6.92 (1H, d, J=6.9 Hz), 7.16 (1H, d, J=1.0 Hz), 7.90 (1H, t, J=1.5 Hz), 9.77 (1H, s), 10.84 (1H, s).

EXAMPLE 5

Ethyl 7-(3-(Aminomethyl)pyrrole-1-yl)-6-chloro-3-oxo-1,2,3,4-tetrahydroquinoxaline-2-carboxylate Hydrochloride

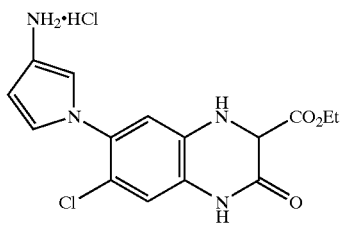

To a solution of the compound of Example 1 (166 mg, 480 μmol) in ethanol (5 ml) were added hydroxylamine hydrochloride (66.7 mg, 960 μmol) and successively sodium acetate (78.7 mg, 960 μmol), and the mixture was refluxed for 3 hours. After cooling, the insolubles were filtered off and solvent was distilled off. The residue obtained was submitted to silica gel column chromatography [dichloromethane-ethanol=10:1] to obtain yellowish brown powder. After dissolved this into ethanol (10 ml), 10% palladium on carbon (containing 51.1% moisture, 50.0 mg) and successively concentrated hydrochloric acid (0.5 ml) were added and the mixture was stirred for 2 hours at room temperature under hydrogen atmosphere (4 Kgf/cm$^2$) (392 KPa). Catalyst was filtered off using celite and solvent was distilled off. Acetone was added to the residue obtained and the crystals were collected by filtration. After washed with acetone, these were air-dried, thereby obtaining 61.2 mg of title compound as colorless powder. Yield 33%.

1H-NMR (DMSO-d6, δ): 1.16 (3H, t, J=7.3 Hz), 3.88–3.92 (2H, m), 4.12–4.17 (2H, m), 4.71 (1H, d, J=2.0 Hz), 6.35 (1H, t, J=2.5 Hz), 6.75 (1H, s), 6.91 (1H, s), 6.93 (1H, t, J=2.4 Hz), 7.03 (1H, s), 7.15 (1H, s), 8.10 (3H, brs), 10.88 (1H, s).

20

EXAMPLE 6

Ethyl 6-Chloro-3,4-dihydro-7-(3-(((4-ethoxycarbonylphenyl)aminocarbonylamino)methyl)pyrrole-1-yl)-3-oxoquinoxaline-2-carboxylate

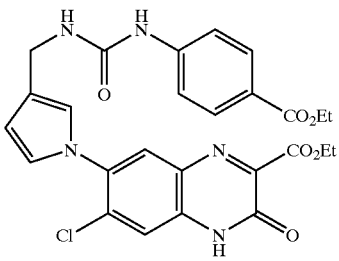

To a solution of the compound of Example 5 (61.2 mg, 159 μmol) in N,N-dimethylformamide (1.6 ml) were added triethylamine (33.3 μl, 239 μmol) and successively ethyl 4-isocyanatobenzoate (36.5 mg, 191 μmol) at room temperature, and the mixture was stirred for 3 hours at the same temperature. Water was added to the reaction mixture and the precipitated crystals were collected by filtration. After washed with water and then with ethyl acetate, these were air-dried, thereby obtaining 27.0 mg of title compound as yellowish brown powder. Yield 32%.

1H-NMR (DMSO-d6, δ): 1.30 (3H, t, J=6.9 Hz), 1.31 (3H, t, J=6.8 Hz), 4.19 (2H, d, J=4.9 Hz), 4.26 (2H, q, J=6.9 Hz), 4.37 (2H, q, J=6.8 Hz), 6.26 (1H, d, J=2.0 Hz), 6.52 (1H, t, J=4.9 Hz), 7.00 (1H, s), 7.01 (1H, s), 7.49 (1H, s), 7.52 (2H, d, J=8.3 Hz), 7.83 (2H, d, J=8.3 Hz), 7.88 (1H, s), 8.89 (1H, s).

EXAMPLE 7

Ethyl 3,4-Dihydro-7-(3-(((4-ethoxycarbonylphenyl)aminocarbonylamino)methyl)pyrrole-1-yl)-6-methoxy-3-oxoquinoxaline-2-carboxylate

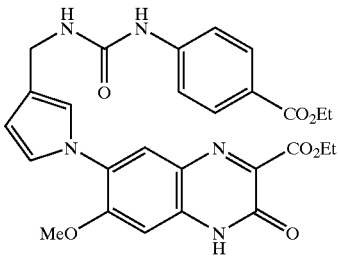

To a solution of the compound of Example 2 (97.1 mg, 284 μmol) in ethanol (3 ml) were added hydroxylamine hydrochloride (39.5 mg, 568 μmol) and successively sodium acetate (46.6 mg, 568 μmol), and the mixture was refluxed for 3 hours. While hot, the insolubles were filtered off using celite and solvent was distilled off. After suspended the residue obtained into ethanol (10 ml), 10% palladium on carbon (20.0 mg) and successively concentrated hydrochloric acid (0.5 ml) were added and the mixture was stirred for 2 hours at room temperature under hydrogen atmosphere (4 atm, 392 KPa). Catalyst was filtered off using celite and solvent was distilled off. Ethyl acetate was added to the residue obtained and the crystals were collected by filtration. After washed with ethyl acetate, these were air-dried, thereby obtaining yellowish brown powder. After dissolved these into N,N-dimethylformaldehyde (3 ml), ethyl 4-isocyanatobenzoate (65.2 mg, 341 μmol) and successively triethylamine (59.4 μl, 426 μmol) were added and the mixture was stirred for 1 hour at 60° C. Triethylamine (396 μl, 2.84 mmol) was added to the reaction mixture, which was stirred further for 3 hours, then solvent was distilled off. The residue obtained was submitted to silica gel column chromatography [dichloromethane-ethanol=20:1] to obtain 59.7 mg of title compound as yellow powder. Yield 39%.

1H-NMR (DMSO-d6, δ): 1.30 (3H, t, J=6.8 Hz), 1.31 (3H, t, J=7.3 Hz), 3.91 (3H, s), 4.17 (2H, d, J=5.4 Hz), 4.26 (2H, q, J=6.9 Hz), 4.35 (2H, q, J=7.3 Hz), 6.21 (1H, d, J=2.0 Hz), 6.50 (1H, t, J=5.4 Hz), 6.96 (1H, s), 7.05 (1H, s), 7.06 (1H, s), 7.52 (2H, d, J=8.8 Hz), 7.74 (1H, s), 7.83 (2H, d, J=8.8 Hz), 8.86 (1H, s), 12.89 (1H, brs).

EXAMPLE 8

Ethyl 3,4-Dihydro-7-(3-(((4-ethoxycarbonylphenyl)aminocarbonylamino)methyl)pyrrole-1-yl)-6-methyl-3-oxoquinoxaline-2-carboxylate

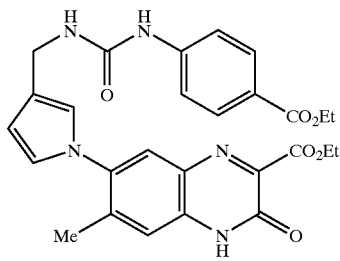

Using the compound (655 mg, 2.00 mmol) of Example 3 and through the process similar to Example 7, 233 mg of title compound were obtained as pale yellow powder. Yield 22%.

1H-NMR (DMSO-d6, δ): 1.30 (3H, t, J=6.9 Hz), 1.31 (3H, t, J=6.9 Hz), 2.27 (3H, s), 4.20 (2H, d, J=5.4 Hz), 4.26 (2H, q, J=7.3 Hz), 4.36 (2H, q, J=7.3 Hz), 6.24 (1H, d, J=2.0 Hz), 6.50 (1H, t, J=5.4 Hz), 6.94 (1H, s), 6.95 (1H, s), 7.27 (1H, s), 7.52 (2H, d, J=8.8 Hz), 7.76 (1H, s), 7.83 (2H, d, J=8.8 Hz), 8.88 (1H, s).

EXAMPLE 9

Ethyl 3,4-Dihydro-7-(3-(((4-ethoxycarbonylphenyl)aminocarbonylamino)methyl)pyrrole-1-yl)-6-fluoro-3-oxoquinoxaline-2-carboxylate

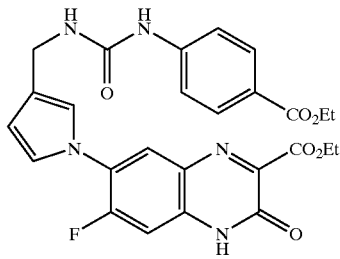

Using the compound (331 mg, 999 μmol) of Example 4 and through the process similar to Example 7, 37.2 mg of title compound were obtained as yellowish brown powder. Yield 7%.

1H-NMR (DMSO-d6, δ): 1.30 (3H, t, J=7.3 Hz), 1.32 (3H, t, J=6.9 Hz), 4.19 (2H, d, J=4.9 Hz), 4.26 (2H, q, J=7.3 Hz), 4.37 (2H, q, J=7.3 Hz), 6.29 (1H, d, J=2.0 Hz), 6.54 (1H, t, J=5.4 Hz), 7.17 (2H, q, J=2.0 Hz), 7.25 (1H, d, J=11.7 Hz), 7.52 (2H, d, J=8.8 Hz), 7.83 (2H, d, J=8.8 Hz), 8.02 (1H, d, J=8.8 Hz), 8.88 (1H, s).

EXAMPLE 10

7-(3-(((4-Carboxyphenyl)aminocarbonylamino)methyl)pyrrole-1-yl)-6-chloro-3,4-dihydro-3-oxoquinoxaline-2-carboxylic Acid

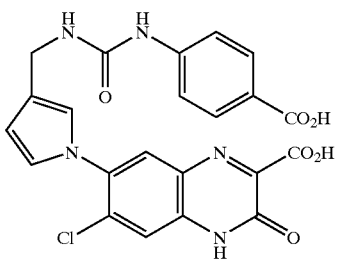

To a solution of the compound (25.4 mg, 47.2 μmol) of Example 6 in ethanol (2 ml) was added 1 mol/L aqueous solution of potassium hydroxide (189 μl, 189 μmol), and the mixture was refluxed for 1.5 hours. After cooling, solvent was distilled off. The residue was dissolved into a small quantity of water, which was brought to pH2 using 4 mol/L hydrochloric acid.

The precipitated crystals were collected by filtration, washed with water, and air-dried, thereby obtaining 18.7 mg of title compound as yellowish brown powder. Yield 77%.

mp>300° C. Anal. Calcd. for $C_{22}H_{16}ClN_5O_6 \cdot 2H_2O$: C, 51.02; H, 3.89; N, 13.52. Found: C, 51.28; H, 3.51; N, 13.52. HR-FAB−: 480.0723 (+1.2 mmu).

EXAMPLE 11

7-(3-(((4-Carboxyphenyl)aminocarbonylamino)methyl)pyrrole-1-yl)-3,4-dihydro-6-methoxy-3-oxoquinoxaline-2-carboxylic Acid

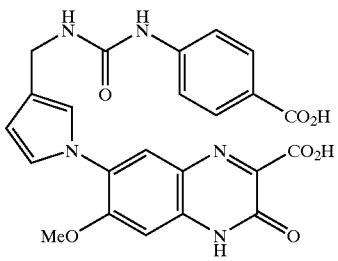

Using the compound (57.7 mg, 108 μmol) of Example 7 and through the process similar to Example 10, 53.2 mg of title compound were obtained as yellowish brown powder. Yield 96%.

mp>300° C. Anal. Calcd. for $C_{23}H_{19}N_5O_7 \cdot 2H_2O$: C, 53.80; H, 4.52; N, 13.64. Found: C, 54.06; H, 4.32; N, 13.32. HR-FAB−: 476.1236 (+3.0 mmu).

EXAMPLE 12

7-(3-(((4-Carboxyphenyl)aminocarbonylamino)methyl)pyrrole-1-yl)-3,4-dihydro-6-methyl-3-oxoquinoxaline-2-carboxylic Acid

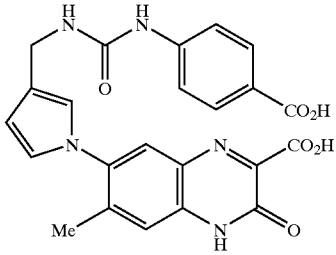

Using the compound (231 mg, 446 μmol) of Example 8 and through the process similar to Example 10, 210 mg of title compound were obtained as yellow powder. Yield 96%.

mp>300° C. Anal. Calcd. for $C_{23}H_{19}N_5O_6 \cdot 3/2H_2O$: C, 56.56; H, 4.54; N, 14.34. Found: C, 56.33; H, 4.20; N, 14.21. HR-FAB–: 460.1236 (–2.1 mmu).

EXAMPLE 13

7-(3-(((4-Carboxyphenyl)aminocarbonylamino)ethyl)pyrrole-1-yl)-3,4-dihydro-6-fluoro-3-oxoquinoxaline-2-carboxylic Acid

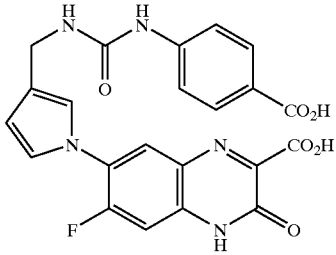

Using the compound (35.5 mg, 68.1 μmol) of Example 9 and through the process similar to Example 10, 25.6 mg of title compound were obtained as yellow powder. Yield 77%.

mp>300° C. Anal. Calcd. for $C_{22}H_{16}FN_5O_6 \cdot 4/3H_2O$: C, 53.99; H, 3.84; N, 14.31. Found: C, 54.10; H, 3.55; N, 14.30. HR-FAB–: 464.0985 (–2.1 mmu).

EXAMPLE 14

Ethyl 6-Chloro-3,4-dihydro-3-oxo-7-(3-((phenylaminocarbonylamino)methyl)pyrrole-1-yl)quinoxaline-2-carboxylate

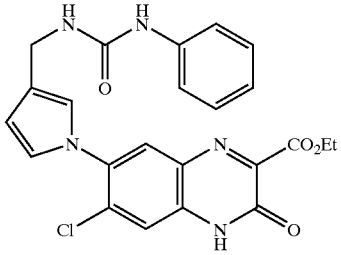

To a solution of the compound (200 mg, 519 μmol) of Example 5 in N,N-dimethylformamide (5 ml) were added phenyl isocyanate (67.6 μl, 622 μmol) and successively triethylamine (108 μl, 778 μmol), and the mixture was stirred for 1 hour at 60° C. Triethylamine (723 μl, 5.19 mmol) was added to the reaction mixture, which was stirred for 4 hours at 100° C. The residue obtained by concentrating the reaction mixture under reduced pressure was submitted to silica gel column chromatography [dichloromethane-ethanol=20:1] to obtain 64.1 mg of title compound as yellow powder. Yield 26%.

1H-NMR (DMSO-d6, δ): 1.32 (3H, t, J=7.3 Hz), 4.18 (2H, d, J=5.4 Hz), 4.38 (2H, q, J=7.3 Hz), 6.26 (1H, t, J=2.0 Hz), 6.33 (1H, t, J=5.4 Hz), 6.88 (2H, t, J=7.3 Hz), 6.999 (1H, s), 7.005 (1H, s), 7.22 (2H, t, J=7.3 Hz), 7.39 (2H, d, J=7.3 Hz), 7.50 (1H, s), 7.88 (1H, s), 8.42 (1H, s), 13.04 (1H, s).

EXAMPLES 15 THROUGH 25

Using the compound of Example 5 and through the process similar to Example 14, compounds listed in following Table 1 were obtained.

TABLE 1

| Example | R |
|---------|---|
| 15 | Ph-3-OMe |
| 16 | Ph-4-Me |
| 17 | Ph-4-Br |
| 18 | Ph-3-Br |
| 19 | Ph-2-Br |
| 20 | Ph-4-CF3 |
| 21 | Ph-3,5-Cl2 |
| 22 | Ph-3-F |
| 23 | Ph-3-NO2 |
| 24 | Ph-3-CO2H |
| 25 | isopropyl |

EXAMPLE 15

1H-NMR (DMSO-d6, δ): 1.31 (3H, t, J=7.3 Hz), 3.70 (3H, s), 4.17 (2H, d, J=5.4 Hz), 4.36 (2H, q, J=7.3 Hz), 6.25 (1H, t, J=2.0 Hz), 6.34 (1H, t, J=5.4 Hz), 6.47 (1H, dd, J=8.3, 2.0 Hz), 6.83–6.86 (1H, m), 6.988 (1H, s), 6.994 (1H, s), 7.11 (1H, t, J=8.3 Hz), 7.16 (1H, t, J=2.0 Hz), 7.47 (1H, s), 7.83 (1H, s), 8.46 (1H, s).

EXAMPLE 16

1H-NMR (DMSO-d6, δ): 1.32 (3H, t, J=7.3 Hz), 2.21 (3H, s), 4.16 (2H, d, J=5.4 Hz), 4.37 (2H, q, J=7.3 Hz), 6.25–6.28 (2H, m), 6.88 (1H, t, J=7.3 Hz), 6.99 (1H, s), 7.00 (1H, s), 7.02 (2H, d, J=8.3 Hz), 7.27 (2H, d, J=8.3 Hz), 7.49 (1H, s), 7.87 (1H, s), 8.31 (1H, s), 13.04 (1H, s).

EXAMPLE 17

1H-NMR (DMSO-d6, δ): 1.32 (3H, t, J=7.3 Hz), 4.17 (2H, d, J=5.4 Hz), 4.38 (2H, q, J=7.3 Hz), 6.25 (1H, d, J=2.0 Hz), 6.40 (1H, t, J=5.4 Hz), 6.996 (1H, s), 7.002 (1H, s), 7.38 (4H, s), 7.49 (1H, s), 7.87 (1H, s), 8.59 (1H, s), 12.80–13.20 (1H, br).

EXAMPLE 18

1H-NMR (DMSO-d6, δ): 1.31 (3H, t, J=7.3 Hz), 4.18 (2H, d, J=5.4 Hz), 4.36 (2H, q, J=7.3 Hz), 6.24 (1H, t, J=2.0 Hz), 6.47 (1H, t, J=5.4 Hz), 6.98 (1H, s), 6.99 (1H, s), 7.06 (1H, dt, J=7.3, 1.5 Hz), 7.15–7.23 (2H, m), 7.46 (1H, s), 7.81 (1H, s), 7.83 (1H, t, J=1.5 Hz), 8.68 (1H, s).

EXAMPLE 19

1H-NMR (DMSO-d6, δ): 1.32 (3H, t, J=7.3 Hz), 4.19 (2H, d, J=5.4 Hz), 4.37 (2H, q, J=7.3 Hz), 6.27 (1H, t, J=2.0 Hz), 6.87–6.91 (1H, m), 7.02 (1H, s), 7.03 (1H, s), 7.26–7.34 (2H, m), 7.50 (1H, s), 7.55 (1H, dd, J=8.3, 1.5 Hz), 7.88 (2H, s), 8.11 (1H, dd, J=8.3, 1.5 Hz), 12.90–13.20 (1H, br).

EXAMPLE 20

1H-NMR (DMSO-d6, δ): 1.32 (3H, t, J=7.3 Hz), 4.20 (2H, d, J=5.4 Hz), 4.37 (2H, q, J=7.3 Hz), 6.26 (1H, d, J=2.0 Hz), 6.52 (1H, t, J=5.4 Hz), 7.00 (1H, s), 7.01 (1H, s), 7.49 (1H, s), 7.57 (2H, d, J=9.3 Hz), 7.62 (2H, d, J=9.3 Hz), 7.87 (1H, s), 8.88 (1H, s), 12.90–13.15 (1H, br).

EXAMPLE 21

1H-NMR (DMSO-d6, δ): 1.31 (3H, t, J=7.3 Hz), 4.18 (2H, d, J=5.4 Hz), 4.37 (2H, q, J=7.3 Hz), 6.25 (1H, d, J=2.0 Hz), 6.62 (1H, t, J=4.9 Hz), 6.99 (1H, s), 7.00 (1H, s), 7.07 (1H, d, J=1.5 Hz), 7.48 (2H, d, J=1.5 Hz), 7.85 (1H, s), 8.87 (1H, s), 12.75–13.25 (1H, br).

EXAMPLE 22

1H-NMR (DMSO-d6, δ): 1.32 (3H, t, J=7.3 Hz), 4.18 (2H, d, J=5.4 Hz), 4.37 (2H, q, J=7.3 Hz), 6.25 (1H, d, J=2.0 Hz), 6.43 (1H, t, J=4.9 Hz), 6.69 (1H, td, J=8.3, 2.0 Hz), 7.00–7.02 (3H, m), 7.23 (1H, t, J=8.3 Hz), 7.45–7.49 (2H, m), 7.87 (1H, s), 8.69 (1H, s), 13.04 (1H, brs).

EXAMPLE 23

1H-NMR (DMSO-d6, δ): 1.31 (3H, t, J=7.3 Hz), 4.21 (2H, d, J=5.4 Hz), 4.36 (2H, q, J=7.3 Hz), 6.26 (1H, d, J=2.0 Hz), 6.60 (1H, t, J=4.9 Hz), 6.995 (1H, s), 7.001 (1H, s), 7.47 (1H, s), 7.51 (1H, t, J=8.3 Hz), 7.64 (2H, dd, J=8.3, 1.5 Hz), 7.74 (2H, dd, J=8.3, 2.0 Hz), 7.83 (1H, s), 8.54 (1H, t, J=2.0 Hz), 9.05 (1H, s), 12.75–13.25 (1H, br).

EXAMPLE 24

1H-NMR (DMSO-d6, δ): 1.29–1.31 (6H, m), 4.19 (2H, d, J=5.4 Hz), 4.30 (2H, q, J=6.9 Hz), 4.37 (2H, q, J=6.9 Hz), 6.26 (1H, d, J=2.0 Hz), 6.39 (1H, t, J=5.4 Hz), 7.000 (1H, s), 7.005 (1H, s), 7.36 (1H, t, J=7.8 Hz), 7.48 (2H, d, J=5.4 Hz), 7.49 (1H, s), 7.61 (1H, dd, J=8.3, 1.0 Hz), 7.87 (1H, s), 8.09 (1H, d, J=2.0 Hz), 8.72 (1H, s), 13.09 (1H, brs).

EXAMPLE 25

1H-NMR (DMSO-d6, δ): 1.02 (6H, d, J=6.9 Hz), 1.32 (3H, t, J=7.3 Hz), 3.60–3.75 (1H, m), 4.07 (2H, d, J=5.4 Hz), 4.38 (2H, q, J=7.3 Hz), 5.66 (2H, d, J=7.8 Hz), 5.87 (1H, t, J=5.4 Hz), 6.19 (1H, dd, J=2.4, 1.5 Hz), 6.92 (1H, s), 6.98 (1H, t, J=2.4 Hz), 7.49 (1H, s), 7.86 (1H, s), 13.04 (1H, brs).

EXAMPLES 26 THROUGH 37

Using the compounds of Examples 14 through 25 and through the process similar to Example 10, compounds listed in following Table 2 were obtained.

TABLE 2

| Example | R |
|---|---|
| 26 | Ph |
| 27 | Ph-3-OMe |
| 28 | Ph-4-Me |
| 29 | Ph-4-Br |
| 30 | Ph-3-Br |
| 31 | Ph-2-Br |
| 32 | Ph-4-CF3 |
| 33 | Ph-3,5-Cl2 |
| 34 | Ph-3-F |
| 35 | Ph-3-NO2 |
| 36 | Ph-3-CO2H |
| 37 | isopropyl |

EXAMPLE 26 mp 171–173° C. (decomposition). Anal. Calcd. for $C_{21}H_{16}ClN_5O_4 \cdot 1/2H_2O$: C, 56.45; H, 3.83; N, 15.67. Found: C, 56.53; H, 3.73; N, 15.61. HR-FAB-: 436.0782 (−1.2 mmu).

EXAMPLE 27 mp 175–177° C. (decomposition). Anal. Calcd. for $C_{22}H_{18}ClN_5O_5 \cdot 4/3H_2O$: C, 53.71; H, 4.20; N, 14.24. Found: C, 53.89; H, 3.91; N, 14.19. HR-FAB-: 466.0896 (−2.2 mmu).

EXAMPLE 28 mp 205–207° C. (decomposition). Anal. Calcd. for $C_{22}H_{18}ClN_5O_4 \cdot 3/2H_2O$: C, 55.18; H, 4.42; N, 14.62. Found: C, 55.21; H, 4.05; N, 14.68. HR-FAB-: 450.0941 (−2.9 mmu).

EXAMPLE 29 mp 204–206° C. (decomposition). Anal. Calcd. for $C_{21}H_{15}BrClN_5O_4 \cdot 1/2H_2O$: C, 47.89; H, 3.07; N, 13.32. Found: C, 47.91; H, 3.01; N, 13.21. HR-FAB-: 513.9947 (+2.9 mmu).

EXAMPLE 30 mp 197–199° C. (decomposition). Anal. Calcd. for $C_{21}H_{15}BrClN_5O_4 \cdot 4/3H_2O$: C, 46.64; H, 3.23; N, 12.95. Found: C, 46.85; H, 3.09; N, 12.86. HR-FAB-: 513.9939 (+2.1 mmu).

EXAMPLE 31 mp 192–194° C. (decomposition). Anal. Calcd. for $C_{21}H_{15}BrClN_5O_4 \cdot H_2O$: C, 47.17; H, 3.20; N, 13.10. Found: C, 47.29; H, 3.12; N, 13.10. HR-FAB-: 513.9939 (+2.1 mmu).

EXAMPLE 32 mp 235–237° C. (decomposition). Anal. Calcd. for $C_{22}H_{15}ClF_3N_5O_4 \cdot H_2O$: C, 50.44; H, 3.27; N, 13.37. Found: C, 50.20; H, 3.09; N, 13.26. HR-FAB-: 504.0684 (−0.3 mmu).

EXAMPLE 33 mp 221–223° C. (decomposition). HR-FAB–: 504.0005 (–2.8 mmu).

EXAMPLE 34 mp 209–211° C. (decomposition). Anal. Calcd. for $C_{21}H_{15}ClFN_5O_4.3/2H_2O$: C, 52.24; H, 3.76; N, 14.50. Found: C, 52.48; H, 3.46; N, 14.28. HR-FAB–: 454.0726 (–2.8 mmu).

EXAMPLE 35 mp 224–226° C. (decomposition). HR-FAB–: 481.0658 (–0.5 mmu).

EXAMPLE 36 mp 217–219° C. (decomposition). Anal. Calcd. for $C_{22}H_{16}ClN_5O_6.3/2H_2O$: C, 51.93; H, 3.76; N, 13.76. Found: C, 52.01; H, 3.43; N, 13.70. HR-FAB–: 480.0703 (–0.7 mmu).

EXAMPLE 37 mp 158–160° C. (decomposition). Anal. Calcd. for $C_{18}H_{18}ClN_5O_4.4/5H_2O$: C, 51.69; H, 4.72; N, 16.75. Found: C, 51.75; H, 4.62; N, 16.46. HR-FAB–: 402.0970 (+0.1 mmu).

EXAMPLE 38

6-Chloro-3,4-dihydro-7-(3-(((4-methoxyphenyl)aminocarbonylamino)methyl)pyrrole-1-yl)-3-oxoquinoxaline-2-carboxylic Acid

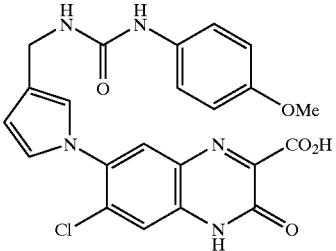

To a solution of the compound (200 mg, 519 μmol) of Example 5 in N,N-dimethylformamide (5 ml) were added 4-methoxyphenyl isocyanate (80.6 μl, 622 μmol) and successively triethylamine (108 μl, 778 μmol), and the mixture was stirred for 1 hour at 60° C. Triethylamine (723 μl, 5.19 mmol) was added to the reaction mixture, which was stirred further for 4 hours. The residue obtained by concentrating the reaction mixture under reduced pressure was submitted to silica gel column chromatography [dichloromethane-ethanol=20:1] to obtain 41.2 mg of yellow powder. After suspended this into ethanol (2 ml), 1 mol/L aqueous solution of potassium hydroxide (332 μl, 332 μmol) was added and the mixture was refluxed for 1 hour. After cooling, solvent was distilled off and the residue was dissolved into a small quantity of water, which was brought to pH2 using 4 mol/L hydrochloric acid. The precipitated crystals were collected by filtration, washed with water, and then air-dried, thereby obtaining 12.1 mg of title compound as yellowish brown powder. Yield 5%.

mp 208–210° C. (decomposition). Anal. Calcd. for $C_{22}H_{18}ClN_5O_5.H_2O$: C, 54.38; H, 4.15; N, 14.41. Found: C, 54.24; H, 4.14; N, 14.30. HR-FAB–: 466.0900 (–1.9 mmu).

EXAMPLE 39

6-Chloro-7-(3-(((4-chlorophenyl)aminocarbonylamino)methyl)pyrrole-1-yl)-3,4-dihydro-3-oxoquinoxaline-2-carboxylic Acid

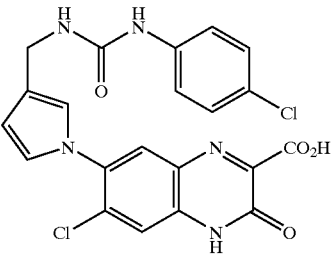

Using the compound (200 mg, 519 μmol) of Example 5 and 4-chlorophenyl isocyanate (80.6 μl, 622 μmol) and through the process similar to Example 38, 44.6 mg of title compound were obtained as yellowish brown powder. Yield 18%.

mp 193–195° C. (decomposition). Anal. Calcd. for $C_{21}H_{15}Cl_2N_5O_4.H_2O$: C, 51.44; H, 3.49; N, 14.28. Found: C, 51.38; H, 3.38; N, 14.11. HR-FAB–: 470.0403 (–2.0 mmu).

EXAMPLE 40

6-Chloro-3,4-dihydro-7-(3-(((1-naphthyl)aminocarbonylamino)methyl)pyrrole-1-yl)-3-oxoquinoxaline-2-carboxylic Acid

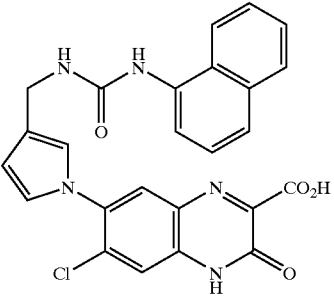

Using the compound (200 mg, 519 μmol) of Example 5 and 1-naphthyl isocyanate (89.4 μl, 622 μmol) and through the process similar to Example 38, 57.1 mg of title compound were obtained as yellowish brown powder. Yield 22%.

mp 196–198° C. Anal. Calcd. for $C_{25}H_{18}ClN_5O_4.4/5H_2O$: C, 59.78; H, 3.93; N, 13.94. Found: C, 60.03; H, 4.01; N, 13.65. HR-FAB–: 486.0986 (–2.0 mmu).

EXAMPLE 41

Ethyl 6-Chloro-3,4-dihydro-7-(4-(hydroxymethyl)imidazole-1-yl)-3-oxoquinoxaline-2-carboxylate

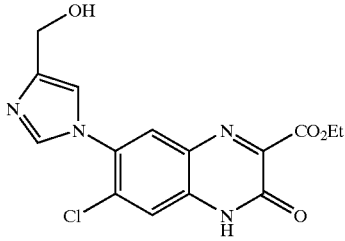

To a solution of ethyl 6-chloro-3-ethoxy-7-(4-(hydroxymethyl)imidazole-1-yl)quinoxaline-2-carboxylate (Referential example 14: 840 mg, 2.23 mmol) in ethanol (50 ml) was added concentrated hydrochloric acid (5 ml), and, employing the Dean-Stark refluxing apparatus equipped with molecular sieves 4A, the mixture was refluxed while dewatering. After cooling, the insolubles were filtered off, solvent was distilled off, and cold ethanol was added to the residue obtained. The precipitated crystals were collected by filtration, washed with cold ethanol, and then air-dried, thereby obtaining 537 mg of title compound as light brown powder. The filtrate and washings were combined and concentrated under reduced pressure. The residue obtained was washed with ethanol and then air-dried, thereby obtaining additional 77.0 mg. Total yield 614 mg. Yield 78%.

1H-NMR (DMSO-d6, δ): 1.32 (3H, t, J=6.8 Hz), 4.39 (2H, q, J=6.8 Hz), 4.59 (2H, s), 7.61 (1H, s), 7.87 (1H, s), 8.34 (1H, s), 9.26 (1H, s), 13.26 (1H, s).

EXAMPLE 42

Ethyl 6-Chloro-3,4-dihydro-3-oxo-7-(4-((phenylcarbamoyloxy)methyl)imidazole-1-yl)quinoxaline-2-carboxylate

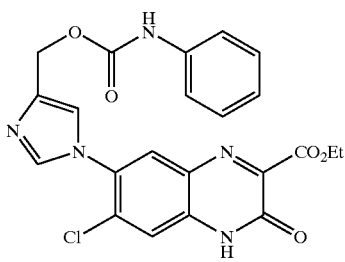

To a suspension of the compound (100 mg, 287 μmol) of Example 41 in ethyl acetate (3 ml) were added phenyl isocyanate (68.4 mg, 574 μmol) and triethylamine (58.1 mg, 574 μmol), and the mixture was refluxed for 24 hours. After cooling, the insolubles were filtered off and solvent was distilled off. The residue obtained was purified by means of silica gel column chromatography [ethyl acetate], thereby obtaining 76.0 mg of title compound as light brown powder. Yield 57%.

1H-NMR (DMSO-d6, δ): 1.31 (3H, t, J=6.8 Hz), 4.37 (2H, q, J=6.8 Hz), 5.08 (2H, s), 6.98 (1H, t, J=7.3 Hz), 7.27 (1H, t, J=7.3 Hz), 7.47 (1H, d, J=7.3 Hz), 7.51 (1H, s), 7.59 (1H, s), 7.94 (1H, s), 8.05 (1H, s), 9.77 (1H, s), 13.11 (1H, brs).

EXAMPLES 43 THROUGH 46

Using the compound of Example 41 and through the process similar to Example 42, compounds listed in following Table 3 were obtained.

TABLE 3

| Example | R |
|---|---|
| 43 | 2-Br |
| 44 | 2-F |
| 45 | 2-CF3 |
| 46 | 3-CO2Et |

EXAMPLE 43

1H-NMR (DMSO-d6, δ): 1.32 (3H, t, J=7.3 Hz), 4.38 (2H, q, J=7.3 Hz), 5.07 (2H, s), 7.13 (1H, dt, J=1.5, 7.3 Hz), 7.37 (1H, dt, J=1.5, 7.8 Hz), 7.53–7.54 (2H, m), 7.58 (1H, s), 7.64 (1H, dd, J=1.5, 7.8 Hz), 7.95 (1H, s), 9.10 (1H, s), 3.12 (1H, s, brs).

EXAMPLE 44

1H-NMR (DMSO-d6, δ): 1.32 (3H, t, J=7.3 Hz), 4.37 (2H, q, J=7.3 Hz), 5.09 (2H, s), 7.12–7.24 (3H, m), 7.52 (1H, s), 7.58 (1H, s), 7.63–7.66 (1H, m), 7.95 (1H, s), 8.07 (1H, s), 9.44 (1H, s), 13.10 (1H, brs).

EXAMPLE 45

1H-NMR (DMSO-d6, δ): 1.32 (3H, t, J=7.3 Hz), 4.38 (2H, q, J=7.8 Hz), 5.06 (2H, s), 7.45 (1H, t, J=7.8 Hz), 7.52 (1H, d, J=7.8 Hz), 7.53 (1H, s), 7.56 (1H, s), 7.66–7.73 (2H, m), 7.95 (1H, s), 8.08 (1H, s), 9.21 (1H, s), 13.12 (1H, brs).

EXAMPLE 46

1H-NMR (DMSO-d6, δ): 1.31 (6H, t, J=7.3 Hz), 4.31 (2H, q, J=7.3 Hz), 4.38 (2H, q, J=7.3 Hz), 5.11 (2H, s), 7.43 (1H, t, J=7.8 Hz), 7.53 (1H, s), 7.58–7.61 (2H, m), 7.69 (1H, d, J=7.8 Hz), 7.95 (1H, s), 8.08 (1H, s), 8.18 (1H, s), 10.02 (1H, s), 13.12 (1H, brs).

EXAMPLE 47

6-Chloro-3,4-dihydro-3-oxo-7-(4-((phenylcarbamoyloxy)methyl)imidazole-1-yl)quinoxaline-2-carboxylic Acid

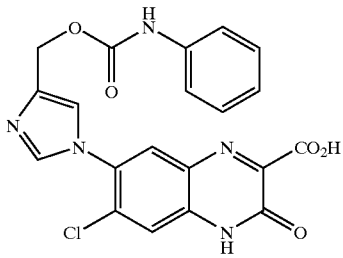

To a solution of the compound (76.0 mg, 162 μmol) of Example 42 in ethanol. (2 ml) were added 1 mol/L aqueous solution of lithium hydroxide (567 μl, 567 μmol) and water (1 ml), and the mixture was stirred for 75 minutes at 50° C. After cooling, water was added to the reaction mixture and the insolubles were filtered off. The filtrate was brought to pH4 with 3 mol/L hydrochloric acid. The precipitated crystals were collected by filtration, washed with water, and then air-dried, thereby obtaining 27.5 mg of title compound as light brown powder. Yield 39%.

mp 199–201° C. (decomposition). HR-FAB+: 440.0755 (−0.6 mmu).

EXAMPLES 48 THROUGH 51

Using the compounds of Example 43 through 46 and through the process similar to Example 47, compounds listed in following Table 4 were obtained.

TABLE 4

| Example | R |
|---|---|
| 48 | 2-Br |
| 49 | 2-F |
| 50 | 2-CF3 |
| 51 | 3-CO2H |

EXAMPLE 48 mp 158–160° C. HR-FAB+: 517.9838 (−2.9 mmu).

EXAMPLE 49 mp 190–192° C. Anal. Calcd. for $C_{20}H_{13}ClFN_5O_5$: C, 46.93; H, 3.74; N, 13.68. Found: C, 47.15; H, 3.55; N, 13.55. HR-FAB+: 458.0690 (+2.3 mmu).

EXAMPLE 50 mp>300° C. HR-FAB+: 508.0646 (+1.1 mmu).

EXAMPLE 51 mp 237–239° C. (decomposition). HR-FAB+: 482.0520 (+1.7 mmu).

EXAMPLE 52

6-Chloro-3,4-dihydro-7-(4-(((4-ethoxycarbonylphenyl)carbamoyloxy)methyl)imidazole-1-yl)-3-oxoquinoxaline-2-carboxylic Acid

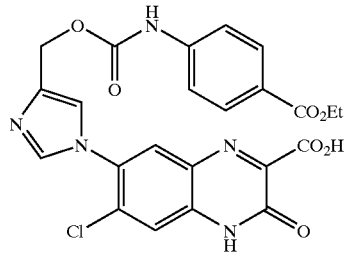

To a solution of ethyl 6-chloro-3-ethoxy-7-(4-(((4-ethoxycarbonylphenyl)carbamoyloxy)methyl)imidazole-1-yl)quinoxaline-2-carboxylate (64.0 mg, 113 μmol) in acetic acid (3 ml) was added 47% hydrobromic acid (0.3 ml), and the mixture was stirred for 3 hours at room temperature. After allowed to stand overnight, the mixture was stirred for 1 hour at 40° C. After cooling, ethanol was added to the residue obtained by concentrating the reaction mixture under reduced pressure. The precipitated crystals were collected by filtration and air-dried, thereby obtaining 18.8 mg of title compound as brown powder. The residue obtained by concentrating the filtrate under reduced pressure was washed with water and air-dried, thereby obtaining additional 37.4 mg. Total yield 56.2 mg. Yield 97%.

1H-NMR (DMSO-d6, δ): 1.30 (3H, t, J=6.8 Hz), 4.28 (2H, q, J=6.8 Hz), 5.13 (2H, s), 7.54 (1H, s), 7.61 (2H, d, J=8.8 Hz), 7.65 (1H, s), 7.89 (2H, d, J=8.8 Hz), 8.06 (1H, s), 8.10 (1H, s), 10.21 (1H, s), 13.12 (1H, brs).

EXAMPLE 53

7-(4-(((4-Carboxyphenyl)carbamoyloxy)methyl)imidazole-1-yl)-6-chloro-3,4-dihydro-3-oxoquinoxaline-2-carboxylic Acid

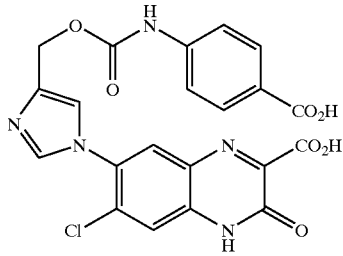

Using the compound (56.0 mg, 109 μmol) of Example 52 and through the process similar to Example 47, 33.4 mg of title compound were obtained as light brown powder. Yield 63%.

mp 246–248° C. (decomposition). HR-FAB−: 482.0520 (+1.7 mmu).

REFERENTIAL EXAMPLE 1

Ethyl (N-(5-Chloro-2-nitrophenyl)carbamoyl)acetate

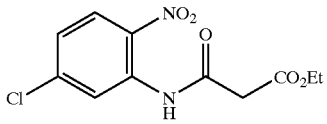

To a solution of 5-chloro-2-nitroaniline (25.4 g, 147 mmol) in N,N-dimethylformamide (300 ml) were added triethylamine (22.6 ml, 162 mmol) and ethyl 3-chloro-3-oxopropionate (20.7 ml, 162 mmol), and the mixture was stirred for 1 hour at room temperature. The reaction mixture was poured into ice water and the precipitated crystals were collected by filtration. These were washed with water and diisopropyl ether in sequence and then air-dried, thereby obtaining 37.1 g of title compound as yellow powder. Yield 88%.

1H-NMR (DMSO-d6, δ): 1.22 (3H, t, J=7.3 Hz), 3.57 (2H, s), 4.14 (2H, q, J=7.3 Hz), 7.47 (1H, dd, J=8.8, 2.0 Hz), 7.94 (1H, d, J=2.4 Hz), 8.06 (1H, d, J=8.8 Hz), 10.69 (1H, s).

REFERENTIAL EXAMPLE 2

Ethyl 6-Chloro-3 4-dihydro-3-oxoquinoxaline-2-carboxylate-1-oxide

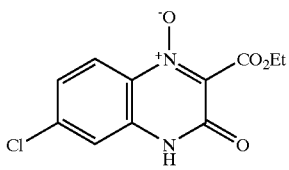

To a solution of the compound (37.1 g, 129 mmol) of Referential example 1 in ethanol (500 ml) was added potassium t-butoxide (29.0 g, 258 mmol) under cooling with ice, and the mixture was stirred for 1 hour at room temperature. After the reaction mixture was neutralized with acetic acid, it was poured into ice water, which was extracted with ethyl acetate. This was dried over anhydrous sodium sulfate and then solvent was distilled off. Diisopropyl ether was added to the residue obtained. The crystals were collected by filtration, washed with diisopropyl ether, and then air-dried, thereby obtaining 13.3 g of title compound as yellowish brown powder. Yield 38%.

1H-NMR (DMSO-d6, δ): 1.31 (3H, t, J=7.3 Hz), 4.39 (2H, q, J=7.3 Hz), 7.40 (1H, d, J=2.4 Hz), 7.43 (1H, dd, J=8.8, 2.5 Hz), 8.12 (1H, d, J=9.3 Hz), 12.60–13.10 (1H, br).

REFERENTIAL EXAMPLE 3

Ethyl 6-Chloro-3,4-dihydro-3-oxoquinoxaline-2-carboxylate

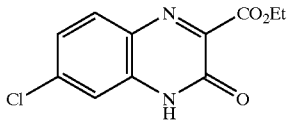

To a solution of the compound (13.3 g, 49.5 mmol) of Referential example 2 in N,N-dimethylformamide (150 ml) was added dropwise phosphorus tribromide (9.40 ml, 99.0 mmol) under cooling with ice, and the mixture was stirred for 1 hour at room temperature. The reaction mixture was poured into ice water. The precipitated crystals were collected by filtration, washed with water and diisopropyl ether in sequence, and then air-dried, thereby obtaining 10.3 g of title compound as light brown powder. Yield 82%.

1H-NMR (DMSO-d6, δ): 1.32 (3H, t, J=7.3 Hz), 4.37 (2H, q, J=7.3 Hz), 7.34 (1H, d, J=2.5 Hz), 7.41 (1H, dd, J=8.8, 2.5 Hz), 7.86 (1H, d, J=8.8 Hz), 12.94 (1H, brs).

REFERENTIAL EXAMPLE 4

Ethyl 6-Chloro-3-ethoxy-7-nitroquinoxaline-2-carboxylate

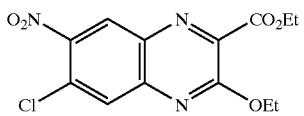

To a solution of the compound (10.3 g, 40.8 mmol) of Referential example 3 in concentrated sulfuric acid (100 ml) was added dropwise concentrated nitric acid (25.9 ml, 408 mmol) under cooling with ice, and the mixture was stirred for 1 hour at room temperature. The reaction mixture was poured into ice water, which was extracted with ethyl acetate. This was dried over anhydrous sodium sulfate and then solvent was distilled off. Silver (I) oxide (18.9 g, 81.6 mmol) was added to the residue obtained and, after suspended into toluene (200 ml), iodoethane (13.0 ml, 163 mmol) was added dropwise at 100° C., which was refluxed for 3 hours. After cooling, the insolubles were filtered off using celite and solvent was distilled off. The residue obtained was submitted to silica gel column chromatography [hexane-ethyl acetate=10:1] to obtain 2.38 g of title compound as yellowish brown oily product. Yield 18%.

1H-NMR (DMSO-d6, δ): 1.47 (3H, t, J=7.3 Hz), 1.51 (3H, t, J=7.3 Hz), 4.54 (2H, q, J=7.3 Hz), 4.64 (2H, q, J=7.3 Hz), 8.01 (1H, s), 8.61 (1H, s).

REFERENTIAL EXAMPLE 5

Ethyl 7-Amino-6-chloro-3,4-dihydro-3-oxoquinoxaline-2-carboxylate

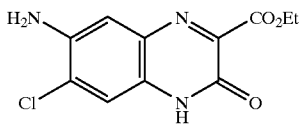

To a solution of the compound (1.85 g, 5.68 mmol) of Referential example 4 in ethanol (60 ml) were added 10% palladium-carbon (containing 51.1% moisture, 200 mg) and successively concentrated hydrochloric acid (3 ml), and the mixture was stirred for 3 hours at room temperature under hydrogen atmosphere (4 atm, 392 KPa). After catalyst was filtered off using celite, solvent was distilled off. Ethyl acetate was added to the residue obtained, the crystals were collected by filtration and air-dried, thereby obtaining 604 mg of title compound as brown powder. Yield 40%.

1H-NMR (DMSO-d6, δ): 1.31 (3H, t, J=7.3 Hz), 4.35 (2H, q, J=7.3 Hz), 5.54 (2H, s), 7.16 (1H, s), 7.26 (1H, s), 12.00–13.00 (1H, br).

REFERENTIAL EXAMPLE 6

Ethyl (N-(2,4-Dinitro-5-methoxyphenyl)carbamoyl) acetate

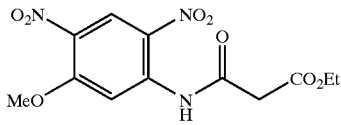

Using 2,4-dinitro-5-methoxyaniline (7.17 g, 36.4 mmol) and through the process similar to Referential example 1, 11.3 g of title compound were obtained as yellowish brown powder. Yield 95%.

1H-NMR (DMSO-d6, δ): 1.35 (3H, t, J=7.3 Hz), 3.63 (2H, s), 4.09 (3H, s), 4.32 (2H, q, J=7.3 Hz), 8.80 (1H, s), 8.99 (1H, s), 11.83 (1H, s).

REFERENTIAL EXAMPLE 7

Ethyl 3,4-Dihydro-6-methoxy-7-nitro-3-oxoquinoxaline-2-carboxylate

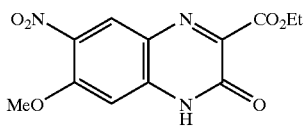

Using the compound (43.6 g, 133 mmol) of Referential example 6 and through the processes similar to Referential examples 2 and 3, 7.26 g of title compound were obtained as light brown powder. Yield 19%.

1H-NMR (DMSO-d6, δ): 1.32 (3H, t, J=7.3 Hz), 4.00 (3H, s), 4.37 (2H, q, J=7.3 Hz), 6.98 (1H, s), 8.43 (1H, s), 13.07 (1H, s).

REFERENTIAL EXAMPLE 8

Ethyl 7-Amino-6-methoxy-3-oxo-1,2,3,4-tetrahydroquinoxaline-2-carboxylate

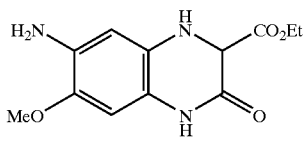

To a suspension of the compound (7.26 g, 24.8 mmol) of Referential example 7 in ethanol (120 ml) was added 10% palladium on carbon (726 mg), and the mixture was stirred for 3 hours at room temperature under hydrogen atmosphere (4 atm, 392 KPa). After dissolved the precipitated crystals into N,N-dimethylformamide, catalyst was filtered off using celite and solvent was distilled off. Ethyl acetate was added to the residue obtained, the crystals were collected by filtration and air-dried. Then, they were washed again using ethanol and air-dried, thereby obtaining 945 mg of title compound as brown powder. Yield 14%.

1H-NMR (DMSO-d6, δ): 1.14 (3H, t, J=7.3 Hz), 3.62 (3H, s), 4.03–4.09 (2H, m), 4.32 (1H, s), 6.10 (1H, s), 6.15 (1H, s), 6.29 (1H, s), 10.07 (1H, s).

REFERENTIAL EXAMPLE 9

Ethyl 3-Ethoxy-6-methyl-7-nitroquinoxaline-2-carboxylate

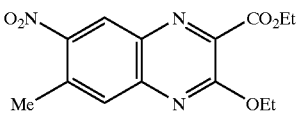

To a solution of 4-methyl-2-phenylenediamine (51.1 g, 418 mmol) in ethanol (500 ml) was added diethyl ketomalonate (76.6 ml, 502 mmol), and the mixture was refluxed for 3 hours. After cooling, the precipitated crystals were collected by filtration, washed with ethanol, and then air-dried, thereby obtaining 77.5 g of a mixture (1:1) of ethyl 3,4-dihydro-6-methyl-3-oxoquinoxaline-2-carboxylate and ethyl 3,4-dihydro-7-methyl-3-oxoquinoxaline-2-carboxylate as yellow needle-like crystals.

To a solution of the mixture (1.00 g, 4.31 mmol) obtained in concentrated sulfuric acid (10 ml) was added dropwise a solution of potassium nitrate (871 mg, 8.62 mmol) in concentrated sulfuric acid (5 ml) at room temperature, and the mixture was stirred for 1 hour at the same temperature. The reaction mixture was poured into ice water. The precipitated crystals were collected by filtration, washed with water, and then air-dried. Silver (I) oxide (2.00 g, 8.62 mmol) was added thereto and, after suspended into toluene (20 ml), iodoethane (1.38 ml, 17.2 mmol) was added dropwise at 100° C., which was refluxed for 4 hours. After cooling, the insolubles were filtered off using celite and solvent was distilled off. The residue obtained was submitted to silica gel column chromatography [hexane-ethyl acetate= 9:1] to obtain 373 mg of title compound as yellow solids.

1H-NMR (CDCl$_3$, δ): 1.43 (3H, t, J=7.3 Hz), 1.51 (3H, t, J=6.8 Hz), 2.78 (3H, s), 4.54 (2H, q, J=7.3 Hz), 4.63 (2H, q, J=6.8 Hz), 7.77 (1H, s), 8.73 (1H, s).

REFERENTIAL EXAMPLE 10

Ethyl 7-Amino-6-methyl-3-oxo-1,2,3,4-tetrahydroquinoxaline-2-carboxylate Hydrochloride

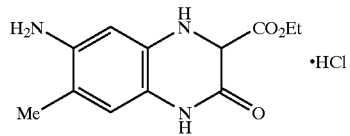

Using the compound (10.0 g, 32.8 mmol) of Referential example 9 and through the process similar to Referential example 5, 7.87 g of title compound were obtained as light brown powder. Yield 84%.

1H-NMR (DMSO-d6, δ): 1.14 (3H, t, J=7.3 Hz), 2.16 (3H, s), 4.06–4.12 (2H, m), 4.56 (1H, s), 6.63 (1H, s), 6.87 (1H, s), 7.01 (1H, brs), 9.97 (3H, brs), 10.68 (1H, s).

REFERENTIAL EXAMPLE 11

Ethyl 7-Amino-6-fluoro-3-oxo-1,2,3,4-tetrahydroquinoxaline-2-carboxylate

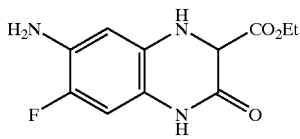

To a solution of 4-fluoro-2-nitroaniline (10 g, 640 mmol) in ethanol (1000 ml) was added 10% palladium on carbon (containing 51.1% moisture, 10.0 g), and the mixture was submitted to hydrogenation reaction at ambient temperature and at ambient pressure. After completion of reaction, catalyst was filtered off using celite and solvent was distilled off. thereby obtaining 4-fluoro-2-phenylenediamine.

Using the phenylenediamine thus obtained and through the process similar to Referential example 9, 14.6 g of a mixture of ethyl 3-ethoxy-6-fluoro-7-nitroquinoxaline-2-carboxylate and ethyl 3-ethoxy-7-fluoro-6-nitroquinoxaline-2-carboxylate were obtained as brown oily product.

Using the mixture (14.0 g, 45.3 mmol) obtained and through the process similar to Referential example 10, 2.03 g of title compound were obtained as brown amorphous material.

1H-NMR (DMSO-d6, δ): 1.14 (3H, t, J=7.3 Hz), 4.05–4.11 (2H, m), 4.39 (1H, d, J=2.0 Hz), 4.69 (2H, brs), 6.21 (1H, d, J=8.8 Hz), 6.37 (1H, d, J=2.0 Hz), 6.42 (1H, d, J=11.3 Hz), 10.17 (1H, s).

REFERENTIAL EXAMPLE 12

Ethyl 6-Amino-3-ethoxy-7-(4-(hydroxymethyl)imidazole-1-yl)quinoxaline-2-carboxylate

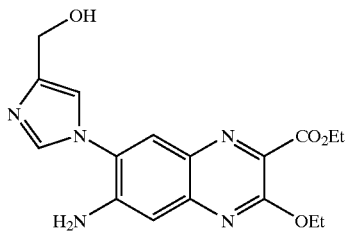

To a solution of ethyl 3-ethoxy-7-(4-(hydroxymethyl)imidazole-1-yl)-6-nitroquinoxaline-2-carboxylate[*A] (2.00 g, 5.16 mmol) in ethanol (200 ml) was added 10% palladium on carbon (200 mg), and the mixture was stirred for 4 hours at room temperature under hydrogen atmosphere (4 atm, 392 KPa). After completion of reaction, N,N-dimethylformamide was added to the reaction mixture to dissolve the precipitated crystals and then catalyst was filtered off using celite. By distilling off solvent, 1.89 g of title compound were obtained as yellow powder. The yield was quantitative.

1H-NMR (DMSO-d6, δ): 1.32 (3H, t, J=7.3 Hz), 1.38 (3H, t, J=7.3 Hz), 4.36 (2H, q, J=7.3 Hz), 4.44–4.51 (4H, m), 4.96 (1H, t, J=5.4 Hz), 6.06 (2H, s), 7.03 (1H, s), 7.28 (1H, s), 7.73 (1H, s), 7.84 (1H, s).

[*A]: WO99/11632, JP10-190109

REFERENTIAL EXAMPLE 13

Ethyl 6-Chloro-3-ethoxy-7-(4-formylimidazole-1-yl)quinoxaline-2-carboxylate

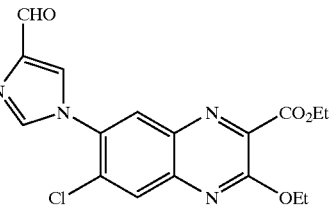

To a solution of cupric chloride (1.07 g, 7.94 mmol) and t-butylnitrite (819 mg, 7.94 mmol) in acetonitrile (70 ml) was added a suspension of the compound (1.89 g, 5.29 mmol) of Referential example 12 in acetonitrile (50 ml), and the mixture was refluxed for 8 hours. After cooling, ethyl acetate was added to the reaction mixture, which was filtered using celite. This was washed with brine, dried using anhydrous magnesium sulfate, and then solvent was distilled off. The residue obtained was purified by means of silica gel column chromatography [hexane-ethyl acetate=3:1] to obtain 1.31 g of title compound as pale yellow powder. Yield 66%.

1H-NMR (DMSO-d6, δ): 1.36 (3H, t, J=7.3 Hz), 1.42 (3H, t, J=7.3 Hz), 4.45 (2H, q, J=7.3 Hz), 4.59 (2H, q, J=7.3 Hz), 8.26 (1H, s), 8.29 (1H, s), 8.48 (1H, s), 8.50 (1H, s), 9.87 (1H, s).

REFERENTIAL EXAMPLE 14

Ethyl 6-Chloro-3-ethoxy-7-(4-(hydroxymethyl)imidazole-1-yl)quinoxaline-2-carboxylate

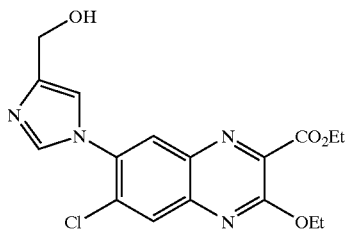

To a solution of the compound (1.31 g, 3.50 mmol) of Referential example 13 in ethanol (50 ml) was added a solution of sodium borohydride (66.2 mg, 1.75 mmol) in ethanol (10 ml), and the mixture was stirred for 3 hours at room temperature. The reaction mixture was concentrated, washed with water, and then air-dried, thereby obtaining 840 mg of title compound as white powder. Yield 64%.

1H-NMR (DMSO-d6, δ): 1.35 (3H, t, J=7.3 Hz), 1.42 (3H, t, J=7.3 Hz), 4.42–4.48 (4H, m), 4.58 (2H, q, J=7.3 Hz), 5.05 (1H, t, J=5.4 Hz), 7.39 (1H, s), 7.94 (1H, s), 8.24 (1H, s), 8.26 (1H, s).

REFERENTIAL EXAMPLE 15

Ethyl 6-Chloro-3-ethoxy-7-(4-(((4-ethoxycarbonylphenyl)carbamoyloxy)methyl)imidazole-1-yl)quinoxaline-2-carboxylate

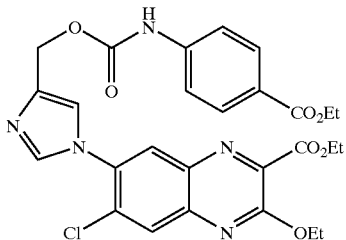

To a solution of the compound (46.0 mg, 122 μmol) of Referential example 14 in tetrahydrofuran (7 ml) was added a ethyl acetate solution of 1 mol/L ethyl 4-isocyanatobenzoate (244 μl, 244 μmol), and the mixture was refluxed for 1 hour. After cooling, the residue obtained by concentrating the reaction mixture under reduced pressure was purified by means of silica gel column chromatography [hexane-ethyl acetate(1:5)→ethyl acetate], thereby obtaining 64.0 mg of title compound as yellow amorphous material. Yield 92%.

1H-NMR (DMSO-d6, δ): 1.30 (3H, t, J=6.8 Hz), 1.35 (3H, t, J=6.8 Hz), 1.42 (3H, t, J=7.3 Hz), 4.28 (2H, q, J=7.3 Hz), 4.44 (2H, q, J=6.8 Hz), 4.58 (2H, q, J=6.8 Hz), 5.12 (2H, s), 7.61 (2H, d, J=8.8 Hz), 7.71 (1H, d, J=1.0 Hz), 7.89 (2H, d, J=8.8 Hz), 8.04 (1H, d, J=1.0 Hz), 8.25 (1H, s), 8.31 (1H, s), 10.22 (1H, s).

[Biological Activity]

Binding Experiment Against AMPA Receptor

To a crude synaptic membranes preparation prepared from cerebral cortex in rat were added [$^3$H]-AMPA (final concentration: 5 nmol/L) that binds selectively to AMPA receptors, potassium thiocyanate (final concentration: 100 mmol/L) and testing compound, and the mixture was incubated for 30 minutes at 0° C. After the reaction was stopped by suction filtration, the radioactivity on filter was measured with liquid scintillation counter. The specific binding level of [$^3$H]-AMPA was determined by subtracting the non-specific binding level in the presence of glutamic acid (0.1 mmol/L) from total binding level. The [$^3$H]-AMPA binding in the absence of testing compound was put on 100, and the concentration of compound to decrease by 50% (IC$_{50}$ value) was determined, which was converted to Ki value to calculate the binding capacity of each compound to AMPA receptor (Eur. J. Pharmacol., 1993, 246, 195–204).

ACTIVITY TABLE A

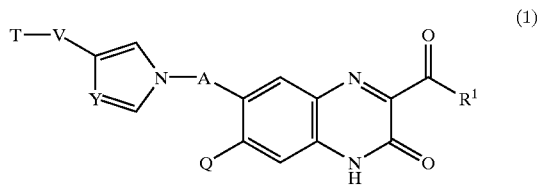

| Testing compound | Q | Y | U | W | [$^3$H]-AMPA (Ki: μmol/L) |
|---|---|---|---|---|---|
| Example 10 | Cl | CH | NH | 4-CO2H—Ph | 0.067 |
| Example 11 | MeO | CH | NH | 4-CO2H—Ph | 0.323 |
| Example 12 | Me | CH | NH | 4-CO2H—Ph | 0.178 |
| Example 13 | F | CH | NH | 4-CO2H—Ph | 0.924 |

[Result]

From the results above, the 6-substituted-7-heteroquinoxalinecarboxylic acid derivatives of the invention are novel compounds with excellent antagonism against excitatory amino acid receptors, in particular, AMPA receptor in non-NMDA receptor.

Since these inventive compounds inhibit the binding of excitatory amino acid receptor that causes the death of nerve cells to AMPA receptor, they are effective for the therapies of disorder of cerebral nerve cells due to excitatory amino acid aforementioned, etc., and can be said to be useful compounds expressing no adverse effects that the drugs with antagonism against NMDA receptor have.

What is claimed is:

1. A 6-substituted-7-heteroquinoxalinecarboxylic acid derivative represented by the formula (1):

(1)

wherein

A denotes a single bond or methylene (CH$_2$),

Y denotes a nitrogen atom or =CH—,

V denotes a single bond or methylene (CH$_2$),

T denotes a hydroxyl group, amino group, lower alkoxycarbonyl group, carboxyl group, aldehyde group, the formula (2):

(2)

$$-O-\underset{H}{\overset{X}{\underset{\|}{C}}}-N-R$$

wherein

X denotes an oxygen atom or sulfur atom,

R denotes an aralkyl group, phenyl group, naphthyl group, 5- or 6-membered heterocycle which may have one or more substituents, 5- or 6-membered heterocycle having a benzene ring fused thereto which may have one or more substituents on the benzene ring or the heterocycle, lower alkyl group which may be substituted with halogen atom, or cycloalkyl group, or the formula (3):

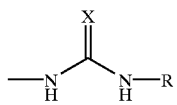

(3)

wherein
X denotes an oxygen atom or sulfur atom,
R denotes an aralkyl group, phenyl group, naphthyl group, 5- or 6-membered heterocycle which may have one or more substituents, 5- or 6-membered heterocycle having a benzene ring fused thereto which may have one or more substituents on the benzene ring or the heterocycle, lower alkyl group which may be substituted with halogen atom, or cycloalkyl group,
Q denotes a halogen atom, lower alkyl group or lower alkoxy group, and
$R^1$ denotes a hydroxyl group or lower alkoxy group,
or an addition salt thereof.

2. The 6-substituted-7-heteroquinoxalinecarboxylic acid derivative of or addition salt thereof of claim 1, wherein
A is a single bond, and
$R^1$ denotes a hydroxyl group or an ethoxy group.

3. The 6-substituted-7-heteroquinoxalinecarboxylic acid derivative of or addition salt thereof of claim 2, wherein
Q denotes a chloro group,
R denotes a hydroxyl group,
V denotes a methylene group,
X denotes an oxygen atom, and
R in the formula (2) and (3) denotes 4-carboxyphenyl.

4. The 6-substituted-7-heteroquinoxalinecarboxylic acid derivative of or addition salt thereof of claim 1, wherein the 5- or 6-membered heterocycle is pyrrolidyl, piperidyl, piperazyl, morpholyl, thiomorpholyl, furanyl, thienyl, pyrazolyl, imidazolyl, oxazolyl, thiazolyl, pyridyl, pyrimidyl, pyridazyl, or pyrazyl.

5. The 6-substituted-7-heteroquinoxalinecarboxylic acid derivative of or addition salt thereof of claim 1, wherein 5- or 6-membered heterocycle having a benzene ring fused thereto is indolyl, tetrahydroquinolyl, benzoxazolidinyl, benzothiazolidinyl, benzofuranyl, benzothienyl, benzimidazolyl, quinolyl, isoquinolyl, quinazolyl, quinoxalyl, or cinnolyl.

6. The 6-substituted-7-heteroquinoxalinecarboxylic acid derivative of or addition salt thereof of claim 1, which is
ethyl 6-chloro-3,4-dihydro-7-(3-formylpyrrole-1-yl)-3-oxoquinoxaline-2-carboxylate,
ethyl 3,4-dihydro-7-(3-formylpyrrole-1-yl)-6-methoxy-3-oxoquinoxaline-2-carboxylate,
ethyl 7-(3-formylpyrrole-1-yl)-6-methyl-3-oxo-1,2,3,4-tetrahydroquinoxaline-2-carboxylate,
ethyl 7-(3-formylpyrrole-1-yl)-6-fluoro-3-oxo-1,2,3,4-tetrahydroquinoxaline-2-carboxylate,
ethyl 7-(3-(aminomethyl)pyrrole-1-yl)-6-chloro-3-oxo-1,2,3,4-tetrahydroquinoxaline-2-carboxylate hydrochloride,
ethyl 6-chloro-7-(3-(((4-ethoxycarbonylphenyl)aminocarbonylamino)methyl)pyrrole-1-yl)-3-oxo-1,2,3,4-tetrahydroquinoxaline-2-carboxylate,
ethyl 6-chloro-3,4-dihydro-7-(3-(((4-ethoxycarbonylphenyl)aminocarbonylamino)methyl)pyrrole-1-yl)-3-oxoquinoxaline-2-carboxylate,
ethyl 6-chloro-3,4-dihydro-7-(3-(((4-ethoxycarbonyl-2-fluorophenyl)aminocarbonylamino)methyl)pyrrole-1-yl)-3-oxoquinoxaline-2-carboxylate,
7-(3-(((4-carboxyphenyl) aminocarbonylamino)methyl)pyrrole-1-yl)-6-chloro-3,4-dihydro-3-oxoquinoxaline-2-carboxylic acid,
7-(3-(((4-carboxyphenyl)aminocarbonylamino)methyl)pyrrole-1-yl)-3,4-dihydro-6-methyl-3-oxoquinoxaline-2-carboxylic acid,
7-(3-(((4-carboxyphenyl)aminocarbonylamino)methyl)pyrrole-1-yl)-3,4-dihydro-6-methoxy-3-oxoquinoxaline-2-carboxylic acid, 7-(3-(((4-carboxyphenyl)aminocarbonylamino)methyl)pyrrole-1-yl)-3,4-dihydro-6-fluoro-3-oxoquinoxaline-2-carboxylic acid,
7-(3-(((4-carboxy-2-fluorophenyl)aminocarbonylamino)methyl)pyrrole-1-yl)-6-chloro-3,4-dihydro-3-oxoquinoxaline-2-carboxylic acid,
ethyl 6-chloro-3,4-dihydro-7-(4-(hydroxymethyl)imidazole-1-yl)-3-oxoquinoxaline-2-carboxylate,
ethyl 6-chloro-3,4-dihydro-7-(4-(((4-ethoxycarbonylphenyl)carbamoyloxy)methyl)imidazole-1-yl)-3-oxoquinoxaline-2-carboxylate,
ethyl 6-chloro-3,4-dihydro-7-(4-(((4-ethoxycarbonylmethylphenyl)carbamoyloxy)methyl)imidazole-1-yl)-3-oxoquinoxaline-2-carboxylate, 7-(4-(((4-carboxyphenyl)carbamoyloxy)methyl)imidazole-1-yl)-6-chloro-3,4-dihydro-3-oxoquinoxaline-2-carboxylic acid,
7-(4-(((4-carboxy-2-fluorophenyl)carbamoyloxy)methyl)imidazole-1-yl)-6-chloro-3,4-dihydro-3-oxoquinoxaline-2-carboxylic acid, 7-(4-(((4-carboxyphenyl)aminocarbonylamino)methyl)imidazole-1-yl)-6-chloro-3,4-dihydro-3-oxoquinoxaline-2-carboxylic acid,
7-(4-(((4-carboxy-2-fluorophenyl)aminocarbonylamino)methyl)imidazole-1-yl)-6-chloro-3,4-dihydro-3-oxoquinoxaline-2-carboxylic acid, or
7-(4-(((4-carboxymethylphenyl)aminocarbonylamino)methyl)imidazole-1-yl)-6-chloro-3,4-dihydro-3-oxoquinoxaline-2-carboxylic acid.

7. The 6-substituted-7-heteroquinoxalinecarboxylic acid derivative of or addition salt thereof of claim 1, which is represented by the formula (1):

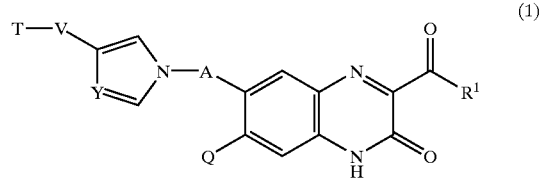

(1)

wherein

A denotes a single bond,
Y denotes a nitrogen atom or =CH—,
V denotes a methylene ($CH_2$), T denotes the formula (2):

$$-O-\underset{H}{\overset{X}{\underset{\|}{C}}}-N-R \quad (2)$$

wherein

X denotes an oxygen atom or sulfur atom,

R denotes an aralkyl group, phenyl group, naphthyl group, 5- or 6-membered heterocycle which may have one or more substituents, 5- or 6-membered heterocycle having a benzene ring fused thereto which may have one or more substituents on the benzene ring or the heterocycle, lower alkyl group which may be substituted with halogen atom, or cycloalkyl group, or the formula (3):

$$-\underset{H}{N}-\underset{\|}{\overset{X}{C}}-\underset{H}{N}-R \quad (3)$$

wherein

X denotes an oxygen atom or sulfur atom,

R denotes an aralkyl group, phenyl group, 5- or 6-membered heterocycle which may have one or more substituents, 5- or 6-membered heterocycle having a benzene ring fused thereto which may have one or more substituents on the benzene ring or the heterocycle, lower alkyl group which may be substituted with halogen atom, or cycloalkyl group, Q denotes a halogen atom, and R¹ denotes a hydroxyl group or lower alkoxy group, or an addition salt thereof.

8. A process for preparing the 6-substituted-7-heteroquinoxalinecarboxylic acid derivative or an addition salt thereof of claim 1, comprising:

oxidizing a compound represented by the formula (4):

(4)

wherein

A denotes a single bond or methylene (CH₂),

Y denotes a nitrogen atom or =CH—,

V denotes a single bond or methylene (CH₂),

T denotes a hydroxyl group, amino group, lower alkoxycarbonyl group, carboxyl group, aldehyde group, the formula (2):

$$-O-\underset{H}{\overset{X}{\underset{\|}{C}}}-N-R \quad (2)$$

wherein

X denotes an oxygen atom or sulfur atom,

R denotes an aralkyl group, phenyl group, naphthyl group, 5- or 6-membered heterocycle which may have one or more substituents, 5- or 6-membered heterocycle having a benzene ring fused thereto which may have one or more substituents on the benzene ring or the heterocycle, lower alkyl group which may be substituted with halogen atom, or cycloalkyl group, or the formula (3):

$$-\underset{H}{N}-\underset{\|}{\overset{X}{C}}-\underset{H}{N}-R \quad (3)$$

wherein

X denotes an oxygen atom or sulfur atom,

R denotes an aralkyl group, phenyl group, naphthyl group, 5- or 6-membered heterocycle which may have one or more substituents, 5- or 6-membered heterocycle having a benzene ring fused thereto which may have one or more substituents on the benzene ring or the heterocycle, lower alkyl group which may be substituted with halogen atom, or cycloalkyl group, Q denotes a halogen atom, lower alkyl group or lower alkoxy group, and R¹ denotes a hydroxyl group or lower alkoxy group.

9. A process for preparing the 6-substituted-7-heteroquinoxalinecarboxylic acid derivative or an addition salt thereof of claim 1, comprising:

hydrolyzing a compound represented by the formula (5)

(5)

wherein

A denotes a single bond or methylene (CH₂),

Y denotes a nitrogen atom or =CH—,

V denotes a single bond or methylene (CH₂),

T denotes a hydroxyl group, amino group, lower alkoxycarbonyl group, carboxyl group, aldehyde group, the formula (2):

$$-O-\underset{H}{\overset{X}{\underset{\|}{C}}}-N-R \quad (2)$$

wherein

X denotes an oxygen atom or sulfur atom, R denotes an aralkyl group, phenyl group, naphthyl group, 5- or 6-membered heterocycle which may have one or more substituents, 5- or 6-membered heterocycle having a benzene ring fused thereto which may have one or more substituents on the benzene ring or the heterocycle, lower alkyl group which may be substituted with halogen atom, or cycloalkyl group, or the formula (3):

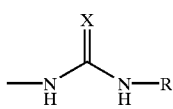

wherein

X denotes an oxygen atom or sulfur atom,

R denotes an aralkyl group, phenyl group, naphthyl group, 5- or 6-membered heterocycle which may have one or more substituents, 5- or 6-membered heterocycle having a benzene ring fused thereto which may have one or more substituents on the benzene ring or the heterocycle, lower alkyl group which may be substituted with halogen atom, or cycloalkyl group, Q denotes a halogen atom, lower alkyl group or lower alkoxy group, $R^1$ denotes a hydroxyl group or lower alkoxy group, and $R^2$ denotes a lower alkyl group which may be substituted with halogen atom, or aralkyl group which may have one or more substituents.

10. A process for preparing the 6-substituted-7-heteroquinoxalinecarboxylic acid derivative or an addition salt thereof of claim 1, wherein Y denotes =CH—, comprising:

reacting a compound represented by the formula (6):

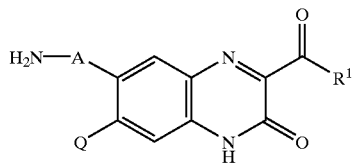

wherein

A denotes a single bond or methylene ($CH_2$),

Q denotes a halogen atom, lower alkyl group or lower alkoxy group, and $R^1$ denotes a hydroxyl group or lower alkoxy group, with a compound represented by the formula (7):

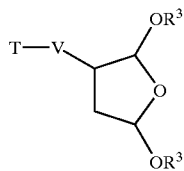

wherein

V denotes a single bond or methylene ($CH_2$),

T denotes a hydroxyl group, amino group, lower alkoxycarbonyl group, carboxyl group, aldehyde group, the formula (2):

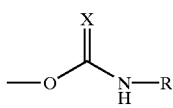

wherein

X denotes an oxygen atom or sulfur atom,

R denotes an aralkyl group, phenyl group, naphthyl group, 5- or 6-membered heterocycle which may have one or more substituents, 5- or 6-membered heterocycle having a benzene ring fused thereto which may have one or more substituents on the benzene ring or the heterocycle, lower alkyl group which may be substituted with halogen atom, or cycloalkyl group, or the formula (3):

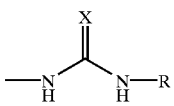

wherein

X denotes an oxygen atom or sulfur atom,

R denotes an aralkyl group, phenyl group, naphthyl group, 5- or 6-membered heterocycle which may have one or more substituents, 5- or 6-membered heterocycle having a benzene ring fused thereto which may have one or more substituents on the benzene ring or the heterocycle, lower alkyl group which may be substituted with halogen atom, or cycloalkyl group, and $R^3$ denotes a lower alkyl group which may be substituted with halogen atom, or aralkyl group which may have one or more substituents.

11. A process for preparing the 6-substituted-7-heteroquinoxalinecarboxylic acid derivative or an addition salt thereof of claim 1, wherein T denotes the formula (2) or the formula (3), comprising:

reacting a compound represented by the formula (8):

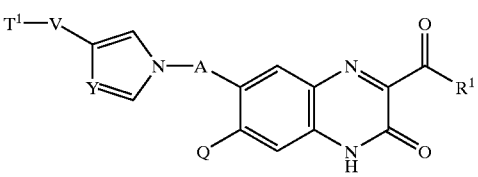

wherein

A denotes a single bond or methylene ($CH_2$),

Y denotes a nitrogen atom or =CH—,

V denotes a single bond or methylene ($CH_2$), $T^1$ denotes a hydroxyl group or amino group, Q denotes a halogen atom, lower alkyl group or lower alkoxy group, and $R^1$ denotes a hydroxyl group or lower alkoxy group, with the ester represented by the formula (9):

Z—N=C=Xa (9)

wherein

Z denotes an aralkyl group, phenyl group, naphthyl group, 5- or 6-membered heterocycle which may have one or more substituents, 5- or 6-membered heterocycle having a benzene ring fused thereto which may have one or more substituents on the benzene ring or the heterocycle, lower alkyl group which may be substituted with halogen atom, or cycloalkyl group, and Xa denotes an oxygen atom or sulfur atom, or with an isocyanic or isothiocyanic ester synthesized from a precursor of said ester represented by the formula (10):

Z—A$_1$—D (10)

wherein
- Z denotes an aralkyl group, phenyl group, naphthyl group, 5- or 6-membered heterocycle which may have one or more substituents, 5- or 6-membered heterocycle having a benzene ring fused thereto which may have one or more substituents on the benzene ring or the heterocycle, lower alkyl group which may be substituted with halogen atom, or cycloalkyl group,
- A$^1$ denotes a single bond, and
- D denotes an amino group, carboxyl group, amide group or lower alkoxycarbonyl group.

12. A process for preparing the 6-substituted-7-heteroquinoxalinecarboxylic acid derivatives or an addition salt thereof of claim 1, wherein R$^1$ denotes a lower alkoxy group, comprising:

reacting a compound represented by the formula (11):

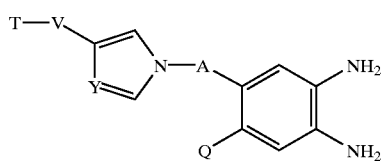
(11)

wherein
- A denotes a single bond or methylene (CH$_2$),
- Y denotes a nitrogen atom or =CH—,
- V denotes a single bond or methylene (CH$_2$),
- T denotes a hydroxyl group, amino group, lower alkoxycarbonyl group, carboxyl group, aldehyde group, the formula (2):

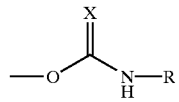
(2)

wherein
- X denotes an oxygen atom or sulfur atom,
- R denotes an aralkyl group, phenyl group, naphthyl group, 5- or 6-membered heterocycle which may have one or more substituents, 5- or 6-membered heterocycle having a benzene ring fused thereto which may have one or more substituents on the benzene ring or the heterocycle, lower alkyl group which may be substituted with halogen atom, or cycloalkyl group, or the formula (3):

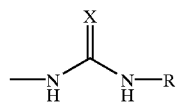
(3)

wherein
- X denotes an oxygen atom or sulfur atom,
- R denotes an aralkyl group, phenyl group, naphthyl group, 5- or 6-membered heterocycle which may have one or more substituents, 5- or 6-membered heterocycle having a benzene ring fused thereto which may have one or more substituents on the benzene ring or the heterocycle, lower alkyl group which may be substituted with halogen atom, or cycloalkyl group, and
- Q denotes a halogen atom, lower alkyl group or lower alkoxy group, with a compound represented by the formula (12):

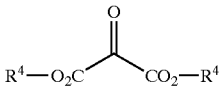
(12)

wherein R$^4$ denotes a lower alkyl group.

13. A compound represented by the formula (4):

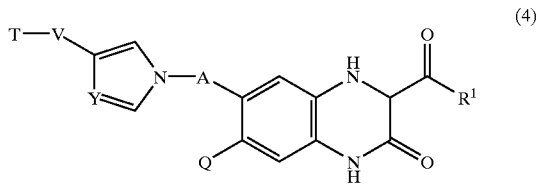
(4)

wherein
- A denotes a single bond or methylene (CH$_2$),
- Y denotes a nitrogen atom or =CH—,
- V denotes a single bond or methylene (CH$_2$),
- T denotes a hydroxyl group, amino group, lower alkoxycarbonyl group, carboxyl group, aldehyde group, the formula (2):

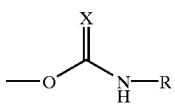
(2)

wherein
- X denotes an oxygen atom or sulfur atom,
- R denotes an aralkyl group, phenyl group, naphthyl group, 5- or 6-membered heterocycle which may have one or more substituents, 5- or 6-membered heterocycle having a benzene ring fused thereto which may have one or more substituents on the benzene ring or the heterocycle, lower alkyl group which may be substituted with halogen atom, or cycloalkyl group, or the formula (3):

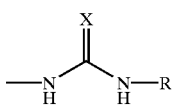
(3)

wherein
- X denotes an oxygen atom or sulfur atom,
- R denotes an aralkyl group, phenyl group, naphthyl group, 5- or 6-membered heterocycle which may have one or more substituents, 5- or 6-membered heterocycle having a benzene ring fused thereto which may have one or more substituents on the benzene ring or the heterocycle, lower alkyl group which may be substituted with halogen atom, or cycloalkyl group,
- Q denotes a halogen atom, lower alkyl group or lower alkoxy group, and $R^1$ denotes a hydroxyl group or lower alkoxy group.

14. A process for preparing the compound of claim 13, wherein Y denotes =CH—, comprising reacting a compound represented by the formula (13)

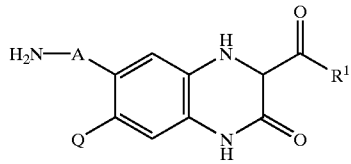
(13)

wherein

A denotes a single bond or methylene ($CH_2$),

Q denotes a halogen atom, lower alkyl group or lower alkoxy group, and $R^1$ denotes a hydroxyl group or lower alkoxy group, with a compound represented by the formula (7):

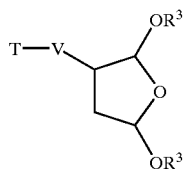
(7)

wherein

V denotes a single bond or methylene ($CH_2$),

T denotes a hydroxyl group, amino group, lower alkoxycarbonyl group, carboxyl group, aldehyde group, the formula (2):

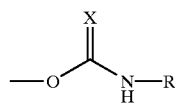
(2)

wherein

X denotes an oxygen atom or sulfur atom,

R denotes an aralkyl group, phenyl group, naphthyl group, 5- or 6-membered heterocycle which may have one or more substituents, 5- or 6-membered heterocycle having a benzene ring fused thereto which may have one or more substituents on the benzene ring or the heterocycle, lower alkyl group which may be substituted with halogen atom, or cycloalkyl group, or the formula (3):

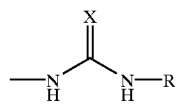
(3)

wherein

X denotes an oxygen atom or sulfur atom,

R denotes an aralkyl group, phenyl group, naphthyl group, 5- or 6-membered heterocycle which may have one or more substituents, 5- or 6-membered heterocycle having a benzene ring fused thereto which may have one or more substituents on the benzene ring or the heterocycle, lower alkyl group which may be substituted with halogen atom, or cycloalkyl group, and $R^3$ denotes a lower alkyl group which may be substituted with halogen atom, or aralkyl group which may have one or more substituents.

15. A process for preparing the compound of claim 13, wherein T denotes the formula (2) or formula (3), comprising:

reacting a compound represented by the formula (14):

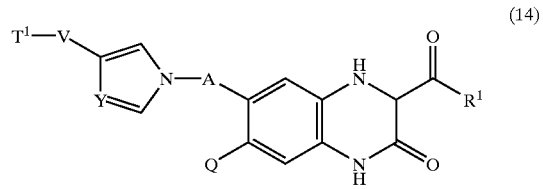
(14)

wherein

A denotes a single bond or methylene ($CH_2$),

Y denotes a nitrogen atom or =CH—,

V denotes a single bond or methylene ($CH_2$), $T^1$ denotes a hydroxyl group or amino group, Q denotes a halogen atom, lower alkyl group or lower alkoxy group, and $R^1$ denotes a hydroxyl group or lower alkoxy group, with an ester represented by the formula (9):

$$Z-N=C=Xa \quad (9)$$

wherein

Z denotes an aralkyl group, phenyl group, naphthyl group, 5- or 6-membered heterocycle which may have one or more substituents, 5- or 6-membered heterocycle having a benzene ring fused thereto which may have one or more substituents on the benzene ring or the heterocycle, lower alkyl group which may be substituted with halogen atom, or cycloalkyl group, and Xa denotes an oxygen atom or sulfur atom, or with an isocyanic or isothiocyanic ester synthesized from a precursor of said ester represented by the formula (10):

$$Z-A_1-D \quad (10)$$

wherein

Z denotes an aralkyl group, phenyl group, naphthyl group, 5- or 6-membered heterocycle which may have one or more substituents, 5- or 6-membered heterocycle having a benzene ring fused thereto which may have one or more substituents on the benzene ring or the heterocycle, lower alkyl group which may be substituted with halogen atom, or cycloalkyl group, $A_1$ denotes a single bond, and D denotes an amino group, carboxyl group, amide group or lower alkoxycarbonyl group.

16. A composition comprising the 6-substituted-7-heteroquinoxalinecarboxylic acid derivative represented by the formula (1) or a salt thereof of claim 1, and a carrier.

* * * * *